United States Patent
Shanahan et al.

(10) Patent No.: US 10,292,394 B2
(45) Date of Patent: May 21, 2019

(54) HERBICIDAL COMPOUNDS

(71) Applicant: Syngenta Participations AG, Basel (CH)

(72) Inventors: Stephen Edward Shanahan, Bracknell (GB); Timothy Jeremiah Cornelius O'Riordan, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/562,947

(22) PCT Filed: Apr. 27, 2016

(86) PCT No.: PCT/EP2016/059381
§ 371 (c)(1),
(2) Date: Sep. 29, 2017

(87) PCT Pub. No.: WO2016/174074
PCT Pub. Date: Nov. 3, 2016

(65) Prior Publication Data
US 2018/0110225 A1  Apr. 26, 2018

(30) Foreign Application Priority Data

Apr. 30, 2015 (GB) .................................. 1507497.4

(51) Int. Cl.
| | |
|---|---|
| *A01N 43/90* | (2006.01) |
| *C07D 471/04* | (2006.01) |
| *C07D 495/04* | (2006.01) |
| *A01N 43/42* | (2006.01) |
| *A01N 43/60* | (2006.01) |
| *A01N 43/76* | (2006.01) |
| *A01N 43/78* | (2006.01) |
| *C07D 401/12* | (2006.01) |
| *C07D 403/12* | (2006.01) |
| *C07D 413/12* | (2006.01) |
| *C07D 417/12* | (2006.01) |
| *C07D 513/04* | (2006.01) |

(52) U.S. Cl.
CPC ............ *A01N 43/90* (2013.01); *A01N 43/42* (2013.01); *A01N 43/60* (2013.01); *A01N 43/76* (2013.01); *A01N 43/78* (2013.01); *C07D 401/12* (2013.01); *C07D 403/12* (2013.01); *C07D 413/12* (2013.01); *C07D 417/12* (2013.01); *C07D 471/04* (2013.01); *C07D 495/04* (2013.01); *C07D 513/04* (2013.01)

(58) Field of Classification Search
CPC ..... C07D 471/04; C07D 495/04; A01N 43/90
See application file for complete search history.

(56) References Cited

U.S. PATENT DOCUMENTS 9,604,983 B2 * 3/2017 Shanahan ............ C07D 471/04

FOREIGN PATENT DOCUMENTS

| WO | WO 2009/090401 | * | 7/2009 |
|---|---|---|---|
| WO | 2010049269 A1 | | 5/2010 |
| WO | 2010130970 A1 | | 11/2010 |
| WO | 2011117151 A1 | | 9/2011 |
| WO | 2011117195 A1 | | 9/2011 |
| WO | 2011117273 A1 | | 9/2011 |
| WO | 2012028580 A1 | | 3/2012 |
| WO | 2012062531 A1 | | 5/2012 |
| WO | 2012085265 A1 | | 6/2012 |

OTHER PUBLICATIONS

International Search Report for International Patent Application No. PCT/EP2016/059381 dated Jun. 1, 2016.
GB Search Report for Application No. GB1507497.4 dated Jan. 14, 2016.

* cited by examiner

*Primary Examiner* — John Pak
(74) *Attorney, Agent, or Firm* — Toni-Junell Herbert; Dinsmore & Shohl LLP

(57) ABSTRACT

The present invention relates to herbicidal heteroarylmethoxy/heterocyclylmethoxy substituted phenyl diones and heteroarylmethoxy/heterocyclylmethoxysubstituted phenyl-dioxo-thiazinone derivatives of formula (I), as well as to processes and intermediates used for the preparation of such derivatives. The invention further extends to herbicidal compositions comprising such derivatives, as well as to the use of such compounds and compositions in controlling undesirable plant growth: in particular the use in controlling weeds, such as broad-leaved dicotyledonous weeds, in crops of useful plants.

15 Claims, No Drawings

HERBICIDAL COMPOUNDS

RELATED APPLICATION INFORMATION

This application is a 371 of International Application No. PCT/EP2016/059381, filed Apr. 27, 2016 which claims priority to GB Application No. 1507497.4, filed Apr. 30, 2015, the contents of which are incorporated herein by reference herein.

The present invention relates to herbicidal heteroarylmethoxy/heterocyclylmethoxy substituted phenyl diones and heteroarylmethoxy/heterocyclylmethoxy substituted phenyl-dioxo-thiazinone derivatives of formula (I), as well as to processes and intermediates used for the preparation of such derivatives. The invention further extends to herbicidal compositions comprising such derivatives, as well as to the use of such compounds and compositions in controlling undesirable plant growth: in particular the use in controlling weeds, such as broad-leaved dicotyledonous weeds, in crops of useful plants.

Herbicidally active naphthyridinones are known from WO2010/049269. In addition, herbicidal diaza-naphthalene derivatives are known from WO2010/130970. WO2012/028580 describes herbicidally active pyridylketosultams. Whilst WO2012/062531 discloses 5H-quinoxaline-6-one derivatives, which exhibit herbicidal activity.

The present invention is based on the finding that heteroarylmethoxy/heterocyclylmethoxy substituted phenyl diones and heteroarylmethoxy/heterocyclylmethoxy substituted phenyl-dioxo-thiazinone derivatives of formula (I) exhibit surprisingly good herbicidal activity.

Thus, in a first aspect there is provided a compound of formula (I)

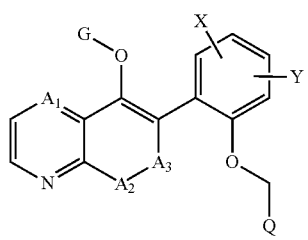

(I)

or a salt or N-oxide thereof,
wherein $A_1$ is $CR^1$ or N;
$R^1$ is hydrogen, $C_1$-$C_4$alkyl, $C_1$-$C_4$haloalkyl, $C_1$-$C_4$alkoxy, $C_1$-$C_4$alkylthio, halogen, cyano, or hydroxyl;
$A_2$ is $CR^{3a}R^{3b}$ or $NR^4$;
$A_3$ is C(O) or S(O)$_2$;
G is hydrogen, or C(O)$R^6$;
X and Y are each independently hydrogen, $C_1$-$C_3$alkyl, $C_1$-$C_3$alkoxy, $C_1$-$C_3$haloalkyl, $C_1$-$C_3$haloalkoxy, or halogen;
$R^{3a}$ and $R^{3b}$ are independently hydrogen, halogen, cyano, $C_1$-$C_8$alkyl, $C_1$-$C_8$alkoxy-$C_1$-$C_4$alkyl-, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkyl-, heterocyclyl, heterocyclyl-$C_1$-$C_4$alkyl-, or $C_1$-$C_8$alkoxycarbonyl-; or $R^{3a}$ and $R^{3b}$ together with the carbon atom they are attached to join to form a 3- to 10-membered carbocyclic ring or a 4- to 10-membered heterocyclic ring;
$R^4$ is hydrogen, $C_1$-$C_{10}$alkyl, $C_1$-$C_4$haloalkyl, $C_2$-$C_{10}$alkenyl, $C_2$-$C_4$haloalkenyl, $C_2$-$C_{10}$alkynyl, $C_2$-$C_4$haloalkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^{10}$, which may be the same or different, or heterocyclyl-$C_1$-$C_6$alkyl- or heterocyclyl-$C_1$-$C_6$alkyl- wherein the heterocyclyl moiety is substituted by one to three $R^{10}$, which may be the same or different;
$R^6$ is selected from the group consisting of $C_1$-$C_6$alkyl, $C_2$-$C_6$alkenyl, $C_2$-$C_6$alkynyl, $C_1$-$C_6$alkyl-S—, —$NR^7R^8$ and phenyl optionally substituted by one or more $R^9$;
$R^7$ and $R^8$ are independently selected from the group consisting of $C_1$-$C_6$alkyl and $C_1$-$C_6$alkoxy, or $R^7$ and $R^8$ together can form a morpholinyl ring; and,
$R^9$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy; and
each $R^{10}$ is independently halogen, $C_1$-$C_4$alkyl, $C_1$-$C_4$haloalkyl, $C_1$-$C_4$alkoxy or $C_1$-$C_4$haloalkoxy;
Q is (i), (ii) or (iii)

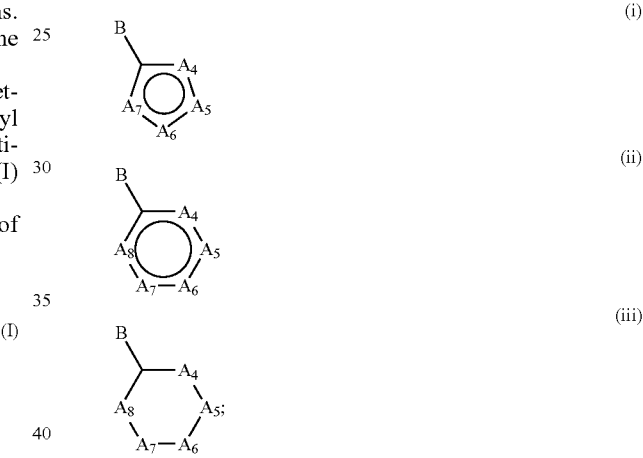

wherein B designates the point of attachment to the rest of the molecule;
$A_4$, $A_5$, $A_6$, $A_7$, and $A_8$, are independently $CR^{11}$, $NR^{12}$, N, S, O, or C(O) provided that at least one and no more than three of $A_4$, $A_5$, $A_6$, $A_7$, and $A_8$ is N, $NR^{12}$, S, O, or C(O);
each $R^{11}$ is independently hydrogen, $C_1$-$C_4$alkyl, $C_1$-$C_4$haloalkyl, halogen, cyano, hydroxyl, $C_1$-$C_4$alkoxy, or $C_1$-$C_4$alkylthio;
each $R^{12}$ is independently hydrogen, $C_1$-$C_4$alkyl, $C_1$-$C_4$haloalkyl, hydroxyl, $C_1$-$C_4$alkoxy, or $C_1$-$C_4$alkylthio.

Compounds of formula (I) may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are di-substituted alkenes, these may be present in (E)- or (Z)-form or as mixtures of both in any proportion.

Compounds of formula (I) may also contain axes of chirality, and may be present as single atropisomers, or pairs of atropisomers in any proportion.

Furthermore, compounds of formula (I) may be in equilibrium with alternative tautomeric forms. For example, a compound of formula (I-i), i.e. a compound of formula (I) wherein $A_2$ is $NR^4$, $R^4$ is hydrogen, $A_3$ is C(O) and G is hydrogen, can be drawn in at least five tautomeric forms:

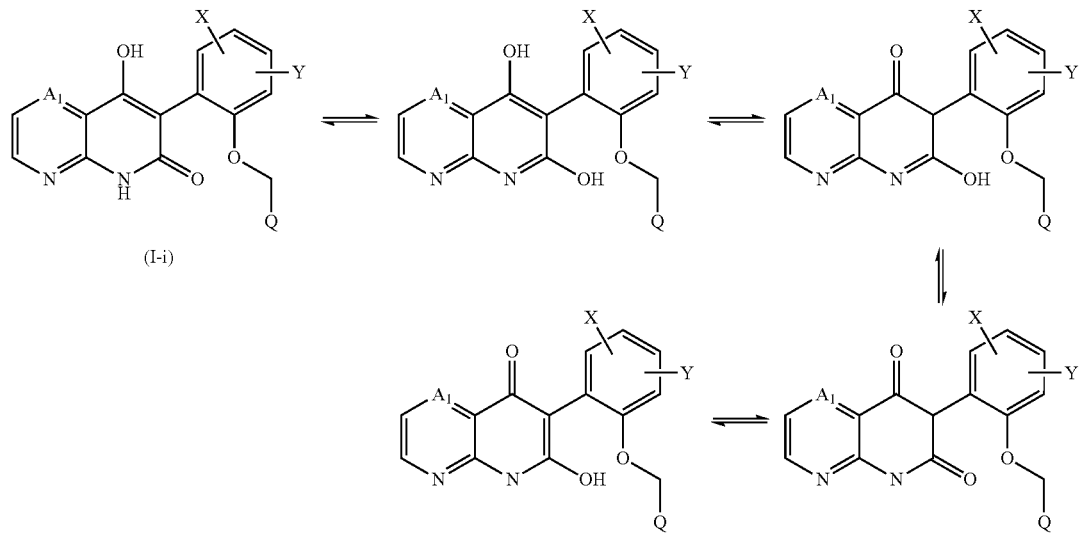

Similarly, a compound of formula (I-ii), i.e. a compound of formula (I) wherein $A_2$ is $NR^4$, $A_3$ is $S(O)_2$ and G is hydrogen, can be drawn in two tautomeic forms:

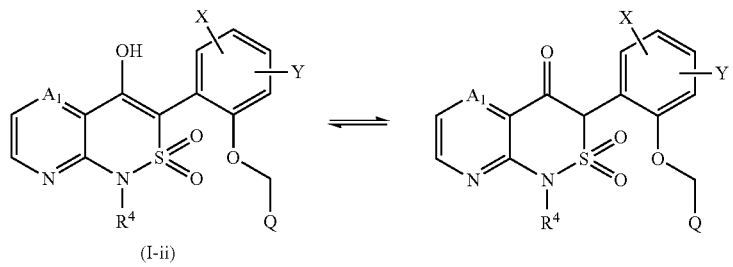

It should be appreciated that all tautomeric forms (single tautomer or mixtures thereof), racemic mixtures and single isomers are included within the scope of the present invention.

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl groups are $C_1$-$C_{10}$alkyl groups (except where already defined more narrowly), but are preferably $C_1$-$C_8$alkyl, $C_1$-$C_6$alkyl, $C_1$-$C_4$alkyl or $C_1$-$C_3$alkyl groups, and, more preferably, are $C_1$-$C_2$alkyl groups (such as methyl). More specifically the alkyl is, for example, methyl, ethyl, n-propyl, isopropyl, n-butyl, sec-butyl, isobutyl, tert-butyl, n-pentyl, neopentyl, or n-hexyl.

Alkenyl and alkynyl moieties can be in the form of straight or branched chains, and the alkenyl moieties, where appropriate, can be of either the (E)- or (Z)-configuration. Typically the alkenyl or alkynyl moieties are $C_2$-$C_{10}$alkenyl or $C_2$-$C_{10}$alkynyl, $C_2$-$C_8$alkenyl or $C_2$-$C_8$alkynyl, $C_2$-$C_6$alkenyl or $C_2$-$C_6$alkynyl, but are preferably $C_2$-$C_4$alkenyl or $C_2$-$C_4$alkynyl, more specifically vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

The cycloalkyl groups generally refer to a $C_3$-$C_{10}$cycloalkyl moiety. Preferably, the term cycloalkyl refers to cyclopropyl, cyclobutyl, cyclopentyl or cyclohexyl.

In the context of the present specification the term "aryl" preferably means phenyl. The term "heteroaryl" as used herein means an aromatic ring system containing at least one ring heteroatom and consists of a single ring. Preferably, single rings will contain 1, 2 or 3 ring heteroatoms selected independently from nitrogen, oxygen and sulfur. Typically "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, or 1,3,5-triazinyl.

Heterocyclyl groups and heterocyclic rings (either alone or as part of a larger group, such as heterocyclyl-alkyl-) are ring systems containing at least one heteroatom and are typically in mono-cyclic form. Preferably, heterocyclyl groups will contain up to two heteroatoms which will preferably be chosen from nitrogen, oxygen and sulfur. Examples of heterocyclic groups include oxetanyl, thietanyl, and azetidinyl. Heterocyclyl groups containing a single oxygen atom as heteroatom are most preferred. The heterocyclyl groups are preferably 4- to 10-membered, more preferably 3- to 8-membered, and more preferably still 3- to 6-membered rings.

Halogen (or halo) encompasses fluorine, chlorine, bromine or iodine. The same correspondingly applies to halogen in the context of other definitions, such as haloalkyl or halophenyl.

Haloalkyl generally refers to groups having a chain length of from 1 to 8 carbon atoms, preferably from 1 to 6 carbon atoms. Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy generally refers to groups having a chain length of from 1 to 8 carbon atoms, preferably from 1 to 6 carbon atoms. Alkoxy is, for example, methoxy, ethoxy, propoxy, isopropoxy, n-butoxy, isobutoxy, sec-butoxy or tert-butoxy, or a pentyloxy or hexyloxy isomer, preferably methoxy and ethoxy. It should also be appreciated that two alkoxy substituents may be present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, or 2,2,2-trichloroethoxy, preferably difluoromethoxy, 2-chloroethoxy or trifluoromethoxy.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-S(O)$_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

The present invention also includes agronomically acceptable salts that the compounds of formula (I) may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of formula (I) according to the invention also include hydrates which may be formed during the salt formation.

Preferred values of $A_1$, $A_2$, $A_3$, $A_4$, $A_5$, $A_6$, $A_7$, $A_8$, $R^1$, $R^{3a}$, $R^{3b}$, $R^4$, $R^6$, $R^7$, $R^8$, $R^9$, $R^{10}$, $R^{11}$, $R^{12}$, G, Q, X, and Y are as set out below, and a compound of formula (I) according to the invention may comprise any combination of said values. The skilled man will appreciate that values for any specified set of embodiments may be combined with values for any other set of embodiments where such combinations are not mutually exclusive.

As defined above, $A_1$ is N or $CR^1$. In one set of embodiments, $A_1$ is N. In a further set of embodiments, $A_1$ is $CR^1$.

Where $A_1$ is $CR^1$, it is preferred that $R^1$ is selected from the group consisting of hydrogen, $C_1$-$C_4$alkyl, $C_1$-$C_4$haloalkyl, $C_1$-$C_4$alkoxy, $C_1$-$C_4$alkylthio, halogen, cyano, and hydroxyl.

More preferably, $R^1$ is hydrogen, $C_1$-$C_3$alkyl, $C_1$-$C_3$alkoxy, halogen, cyano, or hydroxyl. Even more preferably, $R^1$ is hydrogen, $C_1$-$C_3$alkyl, $C_1$-$C_3$alkoxy, or halogen. More preferably still, $R^1$ is hydrogen, fluoro, chloro, bromo, methyl, or methoxy.

In one set of embodiments, $R^1$ is hydrogen, methyl, or methoxy. In a further set of embodiments, $R^1$ is hydrogen, or methoxy.

As stated herein, $A_2$ is either $CR^{3a}R^{3b}$ or $NR^4$.

$R^{3a}$ and $R^{3b}$ are independently hydrogen, halogen, cyano, $C_1$-$C_8$alkyl, $C_1$-$C_8$alkoxy-$C_1$-$C_4$alkyl-, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkyl-, heterocyclyl, heterocyclyl-$C_1$-$C_4$alkyl-, or $C_1$-$C_8$alkoxycarbonyl-; or $R^{3a}$ and $R^{3b}$ together with the carbon atom they are attached to join to form a 3- to 10-membered carbocyclic ring or a 4- to 10-membered heterocyclic ring.

Preferably, $R^{3a}$ and $R^{3b}$ are hydrogen, halogen, $C_1$-$C_8$alkyl, $C_1$-$C_8$haloalkyl or $C_2$-$C_8$alkynyl. Examples of preferred groups for $R^{3a}$ and $R^{3b}$ include fluoro, methyl, ethyl, difluoroethyl and propargyl. In one preferred embodiment, $R^{3a}$ and $R^{3b}$ are each methyl. In a further embodiment, where $R^{3a}$ and $R^{3b}$ together with the carbon atom they are attached to join to form a carbocyclic ring, the carbocyclic ring is preferably cyclopropyl.

Preferably, $R^4$ is hydrogen, $C_1$-$C_{10}$alkyl, $C_1$-$C_4$haloalkyl, $C_2$-$C_{10}$alkenyl, $C_2$-$C_4$haloalkenyl, $C_2$-$C_{10}$alkynyl, $C_2$-$C_4$haloalkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^{10}$, which may be the same or different, or heterocyclyl-$C_1$-$C_6$alkyl- or heterocyclyl-$C_1$-$C_6$alkyl- wherein the heterocyclyl moiety is substituted by one to three $R^{10}$, which may be the same or different.

Preferably, $R^{10}$ is halogen, $C_1$-$C_4$alkyl, $C_1$-$C_4$haloalkyl, $C_1$-$C_4$alkoxy or $C_1$-$C_4$haloalkoxy.

More preferably, $R^4$ is hydrogen, $C_1$-$C_4$alkyl, $C_1$-$C_4$haloalkyl, $C_2$-$C_4$alkenyl, $C_2$-$C_4$haloalkenyl, $C_2$-$C_4$alkynyl or $C_2$-$C_4$haloalkynyl.

In one embodiment, $R^4$ is hydrogen, $C_1$-$C_2$alkyl, $C_1$-$C_2$haloalkyl, $C_2$-$C_3$alkenyl or $C_2$-$C_3$alkynyl. Even more preferably, $R^4$ is hydrogen, $C_1$-$C_2$alkyl, $C_1$-$C_2$haloalkyl or $C_2$-$C_3$alkynyl. More preferably still, $R^4$ is hydrogen, methyl, ethyl, n-propyl, isopropyl, n-butyl, 2-methylpropyl, 2-fluoroethyl, difluoroethyl, trifluoroethyl, allyl, but-3-en-1-yl or propargyl, and most preferably, $R^4$ is hydrogen, methyl, ethyl, difluoroethyl (especially 2,2-difluoroethyl), trifluoroethyl, allyl or propargyl. Examples of such most preferred groups for $R^4$ are hydrogen, methyl, ethyl, 2,2-difluoroethyl or propargyl, especially 2,2-difluoroethyl or propargyl.

As stated herein, $A_3$ is either C(O) or S(O)$_2$. In one set of preferred embodiments, $A_3$ is C(O). In another set of preferred embodiments, $A_3$ is S(O)$_2$.

As described herein, G may be hydrogen or —C(O)—$R^6$, and $R^6$ is selected from the group consisting of $C_1$-$C_6$alkyl, $C_2$-$C_6$alkenyl, $C_2$-$C_6$alkynyl, $C_1$-$C_6$alkyl-S—, $C_1$-$C_6$alkoxy, —NR$^7$R$^8$, and phenyl optionally substituted by one or more $R^9$. As defined herein, $R^7$ and $R^8$ are independently $C_1$-$C_6$alkyl or $C_1$-$C_6$alkoxy; or they can together form a morpholinyl ring. Preferably, $R^7$ and $R^8$ are each independently selected from the group consisting of methyl, ethyl, propyl, methoxy, ethoxy, and propoxy. $R^9$ is selected from the group consisting of halogen, cyano, nitro, $C_1$-$C_3$alkyl, $C_1$-$C_3$haloalkyl, $C_1$-$C_3$alkoxy, and $C_1$-$C_3$haloalkoxy.

Preferably, $R^6$ is $C_1$-$C_6$alkyl, $C_2$-$C_6$alkenyl, $C_2$-$C_6$alkynyl, $C_1$-$C_6$alkyl-S—, —$NR^7R^8$, or phenyl optionally substituted by one or more $R^9$, wherein $R^7$ and $R^8$ together form a morpholinyl ring.

More preferably, $R^6$ is $C_1$-$C_4$alkyl, $C_2$-$C_3$alkenyl, $C_2$-$C_3$alkynyl, $C_1$-$C_3$alkoxy, or —$NR^7R^8$ wherein $R^7$ and $R^8$ together form a morpholinyl ring. More preferably still, $R^6$ is isopropyl, tert-butyl, methyl, ethyl, propargyl, or methoxy.

In one set of embodiments, G is hydrogen or —C(O)—$R^6$, wherein $R^6$ is $C_1$-$C_4$alkyl, $C_2$-$C_3$alkenyl, $C_2$-$C_3$alkynyl, or $C_1$-$C_3$alkoxy. In a further set of embodiments G is hydrogen or —C(O)—$R^6$, wherein $R^6$ is isopropyl, tert-butyl, methyl, ethyl, propargyl, or methoxy. However, it is particularly preferred that G is hydrogen.

Preferably X is $C_1$-$C_3$alkyl, $C_1$-$C_3$alkoxy, $C_1$-$C_3$haloalkyl, $C_1$-$C_3$haloalkoxy, or halogen, more preferably $C_1$-$C_3$haloalkyl or halogen, more preferably still halogen, in particular fluoro, chloro or bromo. Most preferably, X is fluoro or chloro.

In a particularly preferred set of embodiments, X is ortho with respect to the bi-cyclic moiety, and is for example $C_1$-$C_3$haloalkyl or halogen.

Preferably Y is hydrogen, $C_1$-$C_3$alkyl, $C_1$-$C_3$alkoxy, $C_1$-$C_3$haloalkyl, $C_1$-$C_3$haloalkoxy, or halogen, more preferably $C_1$-$C_3$alkyl, $C_1$-$C_3$haloalkyl, or halogen, more preferably still halogen, in particular fluoro, chloro or bromo. Most preferably, Y is fluoro or chloro.

In a particularly preferred set of embodiments, Y is ortho with respect to the Q-$CH_2$—O—moiety, and is for example hydrogen, $C_1$-$C_3$alkyl, $C_1$-$C_3$haloalkyl, or halogen.

As described herein, Q is (i), (ii) or (iii)

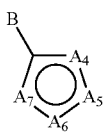
(i)

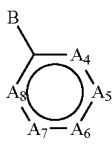
(ii)

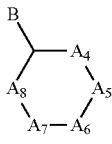
(iii)

wherein $A_4$, $A_5$, $A_6$, $A_7$, and $A_8$, are independently $CR^{11}$, $NR^{12}$, N, S, O, or C(O), provided that at least one and no more than three of $A_4$, $A_5$, $A_6$, $A_7$, and $A_8$ is N, $NR^{12}$, S, O or C(O).

In one embodiment, any two of $A_4$, $A_5$, $A_6$, $A_7$, and $A_8$ are independently N, $NR^{12}$, S, O, or C(O), and all remaining $A_4$, $A_5$, $A_6$, $A_7$, and $A_8$ are $CR^{11}$. In a further embodiment, one of $A_4$, $A_5$, $A_6$, $A_7$, and $A_8$ is independently N and all remaining $A_4$, $A_5$, $A_6$, $A_7$, and $A_8$ are $CR^{11}$.

In certain embodiments, Q is (i) or (ii) and is an optionally substituted pyridyl, thiazolyl, oxazolyl, imidazolyl, isoxazolyl, isothiazolyl, pyrazolyl, pyrazinyl, pyridazinyl, pyrimidyl, or pyridone, and may in particular be an optionally substituted pyridyl, thiazolyl or oxazolyl ring.

For example in one set of embodiments, Q is (i) and is selected from the group consisting of:

(i)-1

(i)-2

(i)-3

(i)-4

(i)-5

(i)-6

(i)-7 and

(i)-8

In a further set of embodiments, Q is (ii) and is selected from the group consisting of:

(ii)-1

(ii)-2

-continued

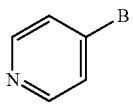 (ii)-3

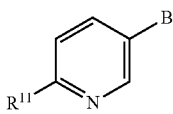 (ii)-4

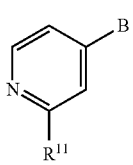 (ii)-5

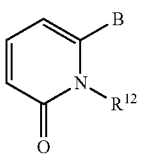 (ii)-6

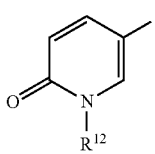 (ii)-7 and

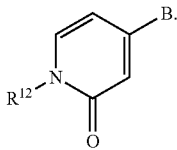 (ii)-8

Preferably, each $R^{11}$ is independently hydrogen, $C_1$-$C_4$alkyl, $C_1$-$C_4$haloalkyl, halogen, cyano, hydroxyl, $C_1$-$C_4$alkoxy, or $C_1$-$C_4$alkylthio. More preferably, $R^{11}$ is hydrogen, methyl, halogen, trifluoromethyl or cyano. Even more preferably, $R^{11}$ is hydrogen, methyl, fluoro, chloro or bromo. More preferably still, $R^{11}$ is hydrogen, methyl or chloro.

Preferably, each $R^{12}$ is independently hydrogen, $C_1$-$C_4$alkyl, $C_1$-$C_4$haloalkyl, hydroxyl, $C_1$-$C_4$alkoxy, or $C_1$-$C_4$alkylthio. More preferably, $R^{12}$ is hydrogen, $C_1$-$C_4$alkyl, hydroxyl or $C_1$-$C_4$alkoxy. Even more preferably, $R^{12}$ is hydrogen or $C_1$-$C_4$alkyl. More preferably still $R^{12}$ is methyl.

In one set of embodiments, Q is selected from 2-pyridyl-, 3-pyridyl-, 4-pyridyl-, 2-thiazolyl-, 4-thiazolyl-, 5-thiazolyl-, pyrazinyl-, 2-pyrimidinyl-, 4-pyrimidinyl-, 5-pyrimidinyl-, 6-methyl-3-pyridyl-, 2-methyl-4-thiazolyl-, 4-methyl-2-thiazolyl-, 2-chloro-4-pyridyl-, 3-pyridazinyl-, 3-pyridazinyl-, 2-methyl-4-oxazolyl-, and 4-methyl-5-oxazolyl-.

In a particularly preferred set of embodiments, $A_1$ is CH or N, $A_2$ is $C(CH_3)_2$ or $NR^4$ where $R^4$ is propargyl or difluoroethyl, X is fluoro or chloro and is ortho with respect to the bicyclic moiety, Y is chloro and is ortho with respect to the Q-$CH_2$O— moiety, and Q is selected from 2-pyridyl-, 3-pyridyl-, 4-pyridyl-, 2-thiazolyl-, 4-thiazolyl-, 5-thiazolyl-, pyrazinyl-, 2-pyrimidinyl-, 4-pyrimidinyl-, 5-pyrimidinyl-, 6-methyl-3-pyridyl-, 2-methyl-4-thiazolyl-, 4-methyl-2-thiazolyl-, 2-chloro-4-pyridyl-, 3-pyridazinyl-, 3-pyridazinyl-, 2-methyl-4-oxazolyl-, and 4-methyl-5-oxazolyl-.

In a further particularly preferred set of embodiments, $A_1$ is CH or N, $A_2$ is $C(CH_3)_2$ or $NR^4$ where $R^4$ is propargyl or difluoroethyl, X is fluoro or chloro and is ortho with respect to the bicyclic moiety, Y is chloro and is ortho with respect to the Q-$CH_2$O— moiety, and Q is selected from 2-pyridyl-, 3-pyridyl-, 4-pyridyl-, 2-thiazolyl-, 4-thiazolyl-, 5-thiazolyl-, pyrazinyl-, 2-pyrimidinyl-, 4-pyrimidinyl-, 5-pyrimidinyl-, 6-methyl-3-pyridyl-, 2-methyl-4-thiazolyl-, 4-methyl-2-thiazolyl-, 2-chloro-4-pyridyl-, 3-pyridazinyl-, 3-pyridazinyl-, 2-methyl-4-oxazolyl-, 4-methyl-5-oxazolyl-, and 2-chloro-5-thiazolyl-.

The compounds in Tables 1 to 22 below illustrate the compounds of the invention.

Table 1:

In Table X below, when X=1, Table 1 provides 20 compounds of formula (I-iii), where Q has the values listed in Table 1. Compounds of formula (I-iii) are compounds of formula (I) where $A_1$ is $CR^1$; $R^1$ and G are each hydrogen; $A_2$ is $NR^4$; $R^4$ is propargyl; $A_3$ is C(O); and X and Y are each chloro.

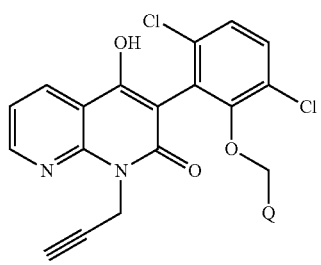 (I-iii)

Table 2:

In Table X below, when X=2, Table 2 provides 20 compounds of formula (I-iv), where Q has the values listed in Table 2. Compounds of formula (I-iv) are compounds of formula (I) where $A_1$ is $CR^1$; $R^1$ and G are each hydrogen; $A_2$ is $NR^4$; $R^4$ is propargyl; $A_3$ is C(O); X is fluoro; and Y is chloro.

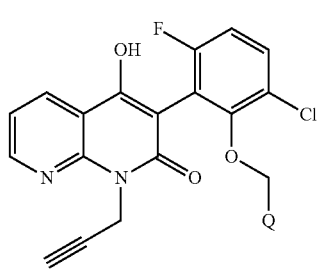 (I-iv)

Table 3:

In Table X below, when X=3, Table 3 provides 20 compounds of formula (I-v), where Q has the values listed in Table 3. Compounds of formula (I-v) are compounds of formula (I) where $A_1$ is $CR^1$; $R^1$ and G are each hydrogen; $A_2$ is $NR^4$; $R^4$ is 2,2-difluoroethyl; $A_3$ is C(O); and X and Y are each chloro.

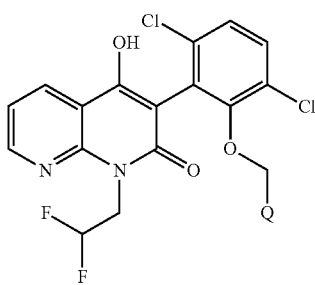
(I-v)

Table 4:

In Table X below, when X=4, Table 4 provides 20 compounds of formula (I-vi), where Q has the values listed in Table 4. Compounds of formula (I-vi) are compounds of formula (I) where $A_1$ is $CR^1$; $R^1$ and G are each hydrogen; $A_2$ is $NR^4$; $R^4$ is 2,2-difluoroethyl; $A_3$ is C(O); X is fluoro; and Y is chloro.

(I-vi)

Table 5:

In Table X below, when X=5, Table 5 provides 20 compounds of formula (I-vii), where Q has the values listed in Table 5. Compounds of formula (I-vii) are compounds of formula (I) where $A_1$ is $CR^1$; $R^1$ and G are each hydrogen; $A_2$ is $NR^4$; $R^4$ is propargyl; $A_3$ is $S(O)_2$; and X and Y are each chloro.

(I-vii)

Table 6:

In Table X below, when X=6, Table 6 provides 20 compounds of formula (I-viii), where Q has the values listed in Table 6. Compounds of formula (I-viii) are compounds of formula (I) where $A_1$ is $CR^1$; $R^1$ and G are each hydrogen; $A_2$ is $NR^4$; $R^4$ is propargyl; $A_3$ is $S(O)_2$; X is fluoro; and Y is chloro.

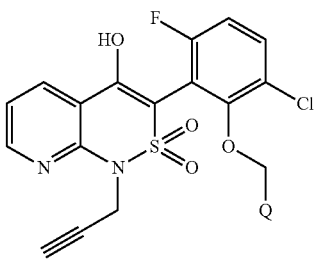
(I-viii)

Table 7:

In Table X below, when X=7, Table 7 provides 20 compounds of formula (I-ix), where Q has the values listed in Table 7. Compounds of formula (I-ix) are compounds of formula (I) where $A_1$ is $CR^1$; $R^1$ and G are each hydrogen; $A_2$ is $CR^{3a}R^{3b}$; $R^{3a}$ and $R^{3b}$ are each methyl; $A_3$ is C(O); and X and Y are each chloro.

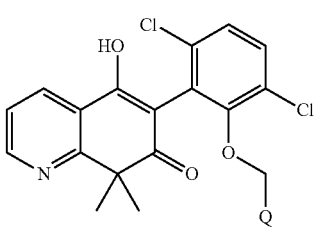
(I-ix)

Table 8:

In Table X below, when X=8, Table 8 provides 20 compounds of formula (I-x), where Q has the values listed in Table 8. Compounds of formula (I-x) are compounds of formula (I) where $A_1$ is $CR^1$; $R^1$ and G are each hydrogen; $A_2$ is $CR^{3a}R^{3b}$; $R^{3a}$ and $R^{3b}$ are each methyl; $A_3$ is C(O); X is fluoro; and Y is chloro.

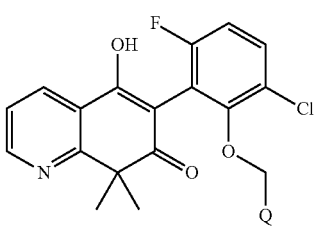
(I-x)

Table 9:

In Table X below, when X=9, Table 9 provides 20 compounds of formula (I-xi), where Q has the values listed in Table 9. Compounds of formula (I-xi) are compounds of formula (I) where $A_1$ is N; G is hydrogen; $A_2$ is $NR^4$; $R^4$ is propargyl; $A_3$ is C(O); and X and Y are each chloro.

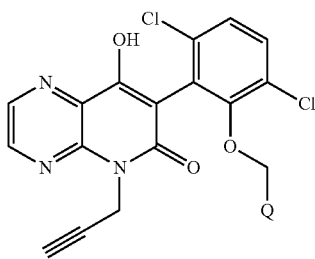

(I-xi)

Table 10:

In Table X below, when X=10, Table 10 provides 20 compounds of formula (I-xii), where Q has the values listed in Table 10. Compounds of formula (I-xii) are compounds of formula (I) where $A_1$ is N; G is hydrogen; $A_2$ is $NR^4$; $R^4$ is propargyl; $A_3$ is C(O); X is fluoro; and Y is chloro.

(I-xii)

Table 11:

In Table X below, when X=11, Table 11 provides 20 compounds of formula (I-xiii), where Q has the values listed in Table 11. Compounds of formula (I-xiii) are compounds of formula (I) where $A_1$ is N; G is hydrogen; $A_2$ is $NR^4$; $R^4$ is 2,2-difluoroethyl; $A_3$ is C(O); and X and Y are each chloro.

(I-xiii)

Table 12:

In Table X below, when X=12, Table 12 provides 20 compounds of formula (I-xiv), where Q has the values listed in Table 12. Compounds of formula (I-xiv) are compounds of formula (I) where $A_1$ is N; G is hydrogen; $A_2$ is $NR^4$; $R^4$ is 2,2-difluoroethyl; $A_3$ is C(O); X is fluoro; and Y is chloro.

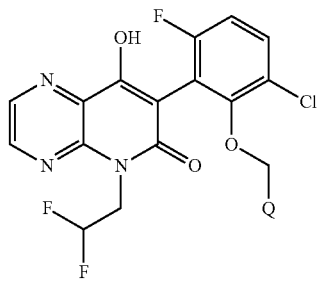

(I-xiv)

Table 13:

In Table X below, when X=13, Table 13 provides 20 compounds of formula (I-xv), where Q has the values listed in Table 13. Compounds of formula (I-xv) are compounds of formula (I) where $A_1$ is N; G is hydrogen; $A_2$ is $NR^4$; $R^4$ is propargyl; $A_3$ is $S(O)_2$; and X and Y are each chloro.

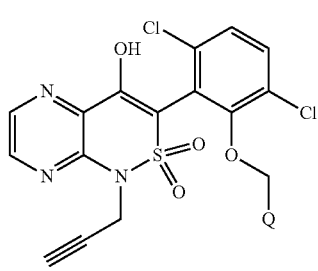

(I-xv)

Table 14:

In Table X below, when X=14, Table 14 provides 20 compounds of formula (I-xvi), where Q has the values listed in Table 14. Compounds of formula (I-xvi) are compounds of formula (I) where $A_1$ is N; G is hydrogen; $A_2$ is $NR^4$; $R^4$ is propargyl; $A_3$ is $S(O)_2$; X is fluoro; and Y is chloro.

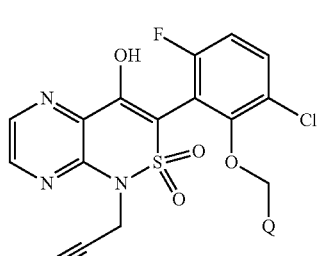

(I-xvi)

Table 15:

In Table X below, when X=15, Table 15 provides 20 compounds of formula (I-xvii), where Q has the values listed in Table 15. Compounds of formula (I-xvii) are compounds of formula (I) where $A_1$ is N; G is hydrogen; $A_2$ is $CR^{3a}R^{3b}$; $R^{3a}$ and $R^{3b}$ are each methyl; $A_3$ is C(O); and X and Y are each chloro.

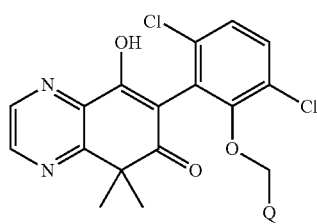
(I-xvii)

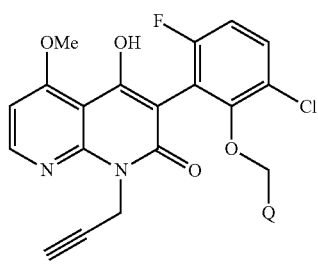
(I-xx)

Table 16:

In Table X below, when X=16, Table 16 provides 20 compounds of formula (I-xviii), where Q has the values listed in Table 16. Compounds of formula (I-xviii) are compounds of formula (I) where $A_1$ is N; G is hydrogen; $A_2$ is $CR^{3a}R^{3b}$; $R^{3a}$ and $R^{3b}$ are each methyl; $A_3$ is C(O); X is fluoro; and Y is chloro.

Table 19:

In Table X below, when X=19, Table 19 provides 20 compounds of formula (I-xxi), where Q has the values listed in Table 19. Compounds of formula (I-xxi) are compounds of formula (I) where $A_1$ is $CR^1$; $R^1$ is methoxy; G is hydrogen; $A_2$ is $NR^4$; $R^4$ is 2,2-difluoroethyl; $A_3$ is C(O); and X and Y are each chloro.

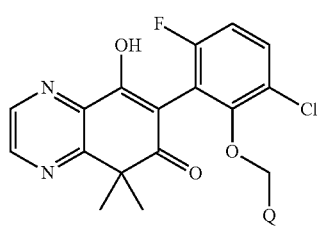
(I-xviii)

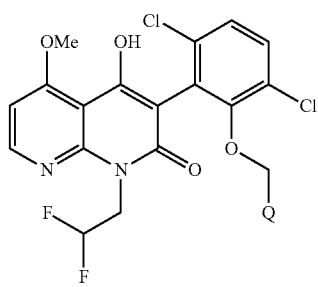
(I-xxi)

Table 17:

In Table X below, when X=17, Table 17 provides 20 compounds of formula (I-xix), where Q has the values listed in Table 17. Compounds of formula (I-xix) are compounds of formula (I) where $A_1$ is $CR^1$; $R^1$ is methoxy; G is hydrogen; $A_2$ is $NR^4$; $R^4$ is propargyl; $A_3$ is C(O); and X and Y are each chloro.

Table 20:

In Table X below, when X=20, Table 20 provides 20 compounds of formula (I-xxii), where Q has the values listed in Table 20. Compounds of formula (I-xxii) are compounds of formula (I) where $A_1$ is $CR^1$; $R^1$ is methoxy; G is hydrogen; $A_2$ is $NR^4$; $R^4$ is 2,2-difluoroethyl; $A_3$ is C(O); X is fluoro; and Y is chloro.

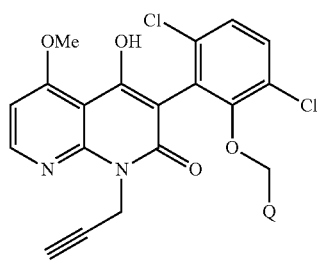
(I-xix)

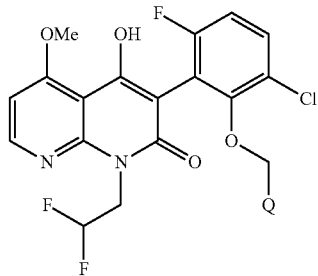
(I-xxii)

Table 18:

In Table X below, when X=18, Table 18 provides 20 compounds of formula (I-xx), where Q has the values listed in Table 18. Compounds of formula (I-xx) are compounds of formula (I) where $A_1$ is $CR^1$; $R^1$ is methoxy; G is hydrogen; $A_2$ is $NR^4$; $R^4$ is propargyl; $A_3$ is C(O); X is fluoro; and Y is chloro.

Table 21:

In Table X below, when X=21, Table 21 provides 20 compounds of formula (I-xxiii), where Q has the values listed in Table 21. Compounds of formula (I-xxiii) are compounds of formula (I) where $A_1$ is N; G is hydrogen; $A_2$ is $CR^{3a}R^{3b}$; $R^{3a}$ and $R^{3b}$ are each methyl; $A_3$ is $S(O)_2$; and X and Y are each chloro.

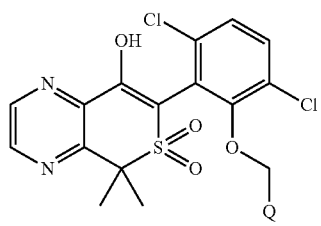

(I-xxiii)

Table 22:

In Table X below, when X=22, Table 22 provides 20 compounds of formula (I-xxiv), where Q has the values listed in Table 22. Compounds of formula (I-xxiv) are compounds of formula (I) where $A_1$ is N; G is hydrogen; $A_2$ is $CR^{3a}R^{3b}$; $R^{3a}$ and $R^{3b}$ are each methyl; $A_3$ is $S(O)_2$; X is fluoro; and Y is chloro.

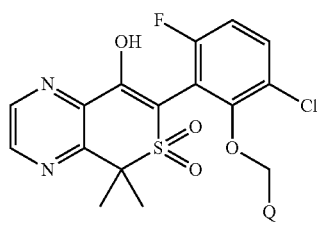

(I-xxiv)

TABLE X

A hyphen or ~ denotes the point of attachment to the rest of the molecule

| Comp. No. | Q |
|---|---|
| X.01 | 2-pyridyl- |
| X.02 | 3-pyridyl- |
| X.03 | 4-pyridyl- |
| X.04 | 2-thiazolyl- |
| X.05 | 4-thiazolyl- |
| X.06 | 5-thiazolyl- |
| X.07 | pyrazinyl- |
| X.08 | 2-pyrimidinyl- |
| X.09 | 4-pyrimidinyl- |
| X.10 | 5-pyrimidinyl- |
| X.11 | 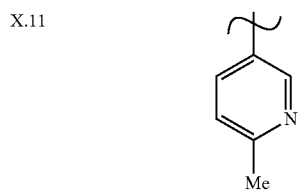 |
| X.12 |  |
| X.13 | 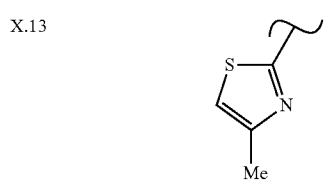 |

TABLE X-continued

A hyphen or ~ denotes the point of attachment to the rest of the molecule

| Comp. No. | Q |
|---|---|
| X.14 | (2-chloro-pyridin-4-yl structure) |
| X.15 | 3-pyridazinyl- |
| X.16 | 4-pyridazinyl- |
| X.17 | (2-methyl-oxazol-4-yl structure) |
| X.18 | (4-methyl-oxazol-5-yl structure) |
| X.19 | (2-chloro-thiazol-5-yl structure) |
| X.20 | (6-chloro-pyridin-3-yl structure) |

The compounds of the present invention may be prepared according to the following schemes, in which the substituents $A_1$, $R^4$ and Q have (unless otherwise stated explicitly) the definitions described hereinbefore.

Scheme 1

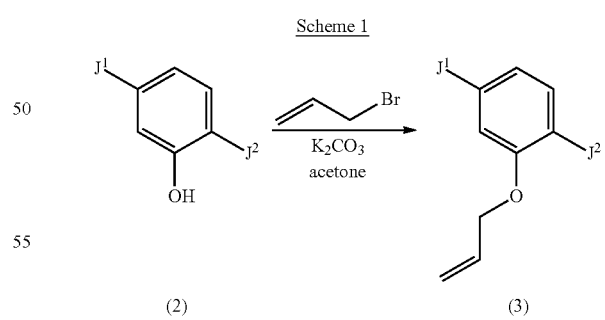

(2)    (3)

1) An allyl ether of formula (3) where $J^1$ and $J^2$ are each independently halogen, $C_1$-$C_3$alkyl or $C_1$-$C_3$haloalkyl, can be made by reacting a phenol of formula (2) with allyl bromide and potassium carbonate in acetone, at a temperature between 0° C. and reflux, as shown in Scheme 1. Many phenols of formula (2) are commercially available [such as 2,5-dichlorophenol or 2-chloro-5-fluoro-phenol] or can be made by methods known to a person skilled in the art.

2) Alternatively, a specific example of an ether of formula (3) as defined in 1), namely 2-allyloxy-1,4-dichloro-benzene, can be made according to *J. Chem. Soc.*, Perkin Trans. 2, 2001, 1824.

Scheme 2

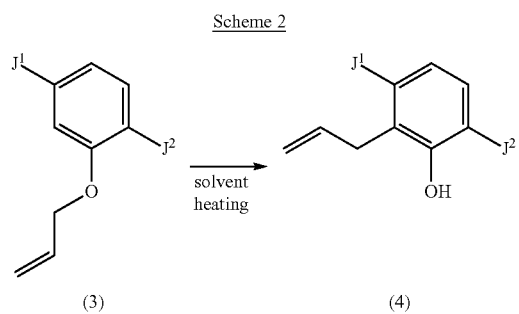

3) A phenol of formula (4) where $J^1$ and $J^2$ are as defined in 1) can be made by heating an ether of formula (3) as defined in 1) in a solvent [such as N,N-dimethylformamide or N,N-dimethylaniline], at a temperature between 100° C. and 200° C., as shown in Scheme 2.

Scheme 3

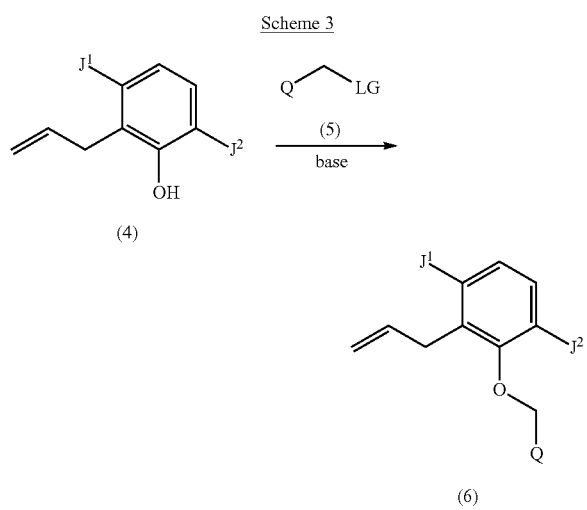

4) An unsaturated ether of formula (6) where $J^1$ and $J^2$ are as defined in 1) can be made by reacting a phenol of formula (4) as defined in 3) with a compound of formula (5), where LG is a leaving group, for example a halide [such as chloride, bromide or iodide], tosylate, mesylate or triflate, in the presence of a base [such as potassium carbonate] in a solvent [such as acetone or acetonitrile] and optionally using heating, as shown in Scheme 3. Many compounds of formula (5) are commercially available [such as 2-(bromomethyl)pyridine, 3-(bromomethyl)pyridine, 2-chloro-5-chloromethylthiazole or 2-(chloromethyl)-1,3-thiazole] or can be made according to Scheme 11.

Scheme 4

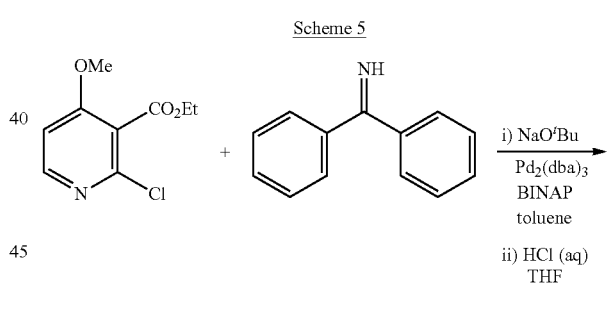

5) A carboxylic acid of formula (7) where $J^1$ and $J^2$ are as defined in 1) can be made by reacting an unsaturated ether of formula (6) as defined in 4) with an oxidising agent [such as ruthenium tetroxide generated in-situ from sodium periodate and ruthenium (III) chloride] in a solvent system [comprising one or more of ethyl acetate, dichloromethane, water and acetonitrile] at a temperature between 0° C. and 50° C., as shown in Scheme 4.

6) A carboxylic acid of formula (7) where $J^1$ and $J^2$ are as defined in 1) can be made by oxidising an unsaturated ether of formula (6) as defined in 4) by a two-stage process, known to the person skilled in the art as ozonolysis followed by Pinnick oxidation, via an intermediate aldehyde.

Scheme 5

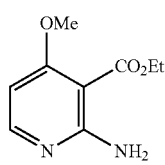

7) ethyl 2-amino-4-methoxy-pyridine-3-carboxylate can be made by amination of ethyl 2-chloro-4-methoxy-pyridine-3-carboxylate as shown in Scheme 5. Ethyl 2-chloro-4-methoxy-pyridine-3-carboxylate can be prepared according to *J. Org. Chem.*, 2005, 70, 6204, and benzophenone-imine is readily available from a variety of commercial sources.

Scheme 6

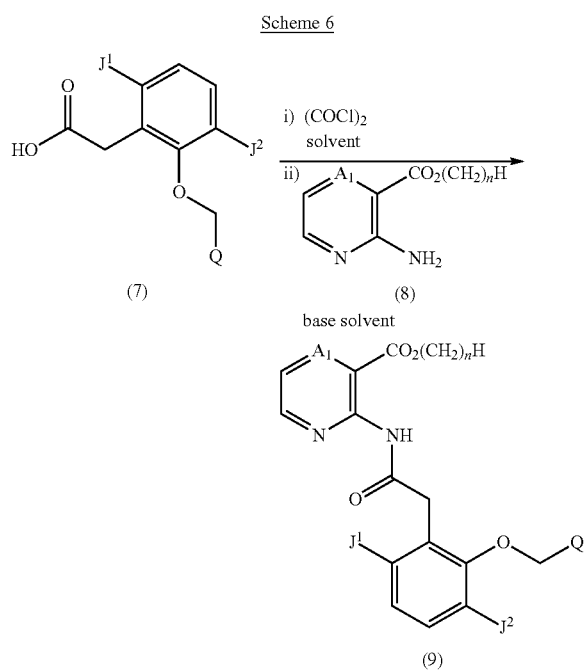

8) An amide of formula (9) where $J^1$ and $J^2$ are as defined in 1) and n is 1 or 2 can be made by activating a carboxylic acid of formula (7) as defined in 5) with oxalyl chloride in a solvent [such as dichloromethane or N,N-dimethylacetamide], optionally including N,N-dimethylformamide as a catalyst, then reacting the intermediate acyl chloride with amino compounds of formula (8) where n=1 or 2, and a base [such as pyridine or triethylamine] in a solvent [such as dichloromethane or N,N-dimethylacetamide] as shown in Scheme 6. An example of an amino-compound of formula (8) is commercially available 2-amino-nicotinic acid ethyl ester. A further example of a compound of formula (8) is methyl 3-aminopyrazine-2-carboxylate, prepared according to WO2005115986(A1), 2005 or U.S. Pat. No. 5,252,538 A1, 1993. A further example of a compound of formula (8) is ethyl 2-amino-4-methoxy-pyridine-3-carboxylate, prepared as shown in Scheme 5. Carboxylic acids of formula (7) are made either according to Scheme 4 or according to Scheme 16.

Scheme 7

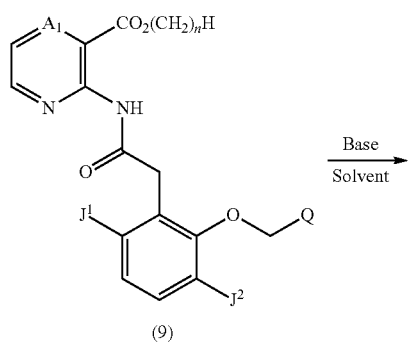

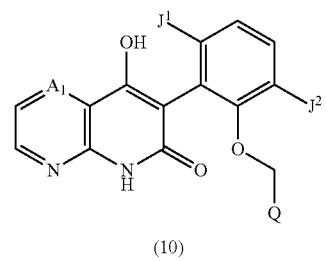

9) A bicyclic hydroxy compound of formula (10) where $J^1$ and $J^2$ are as defined in 1) can be made by reacting an amide of formula (9) as defined in 8) with a base [such as lithium hexamethyldisilazide, sodium hexamethyldisilazide, potassium hexamethyldisilazide or sodium hydride] in a solvent [such as tetrahydrofuran, 1,4-dioxane or toluene] at a temperature between −20° C. and 50° C., as shown in Scheme 7.

Scheme 8

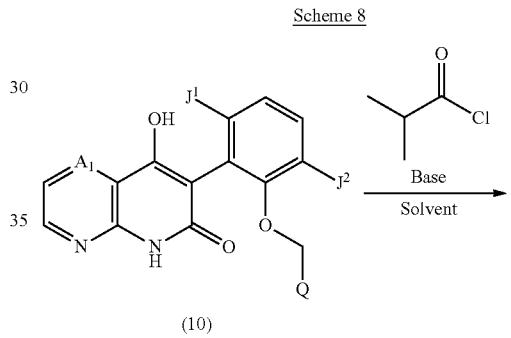

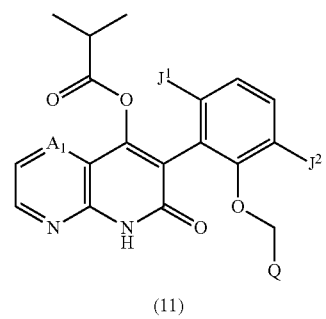

10) An ester of formula (11) where $J^1$ and $J^2$ are as defined in 1) can be made by reacting a bicyclic hydroxy compound of formula (10) as defined in 9) with isobutyryl chloride and a base [such as triethylamine or pyridine] in a solvent [such as dichloromethane, acetonitrile or tetrahydrofuran], optionally including 4-dimethylamino-pyridine (DMAP) as a catalyst, as shown in Scheme 8.

Scheme 9

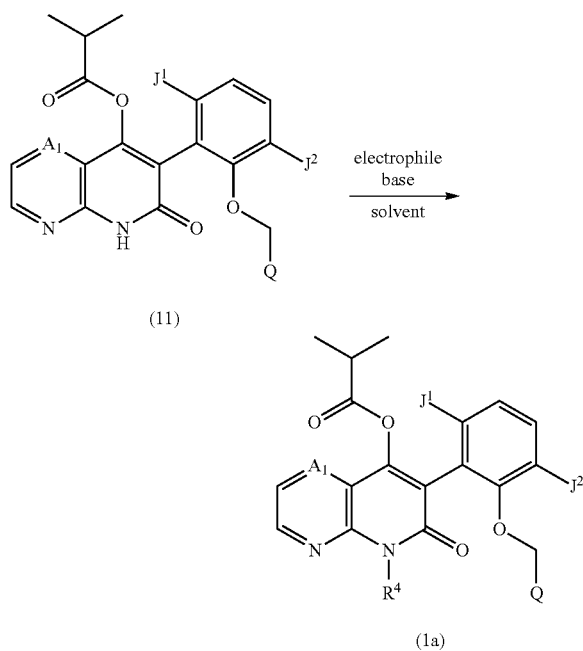

(11)

(1a)

11) An N-alkylated compound of formula (1a) where $J^1$ and $J^2$ are as defined in 1) can be made by reacting an ester of formula (11) as defined in 10) with an electrophilic alkylating agent [such as propargyl bromide or 2,2-difluoroethyl triflate] and a base [such as sodium hydride, diisopropylethylamine or cesium carbonate] in a solvent [such as tetrahydrofuran, acetonitrile or N,N-dimethylformamide], at a temperature between 0° C. and 25° C., as shown in Scheme 9.

Scheme 10

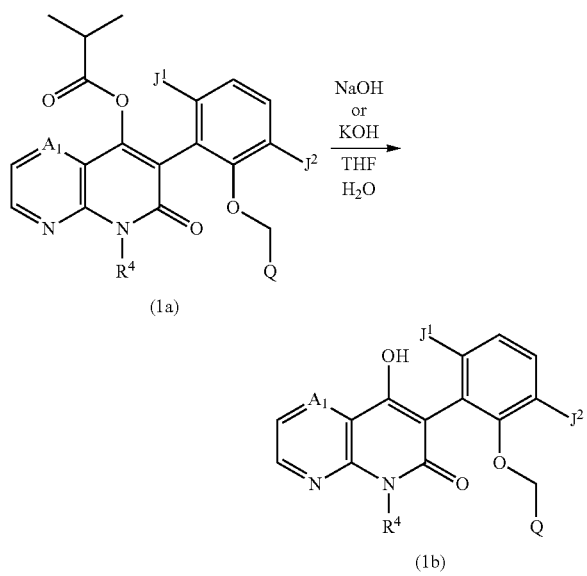

(1a)

(1b)

12) A hydroxy compound of formula (1b) where $J^1$ and $J^2$ are as defined in 1) can be made by reacting an N-alkylated compound of formula (1a) as defined in 11) with sodium hydroxide or potassium hydroxide in aqueous tetrahydrofuran, at a temperature between −10° C. and 100° C., as shown in Scheme 10.

Scheme 11

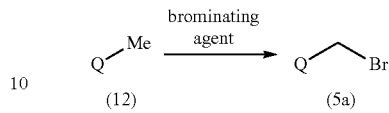

(12)            (5a)

13) Bromides of formula (5a) are examples of compounds of formula (5). A bromide of formula (5a) can be made by reacting a methyl-substituted compound of formula (12) with a brominating agent [such as elemental bromine or N-bromosuccinimide] in a solvent [such as carbon tetrachloride, benzotrifluoride or dichloromethane] optionally using heating, optionally including a radical initiator [such as benzoyl peroxide or 2,2'-azobis(2-methylpropionitrile)], and optionally irradiating the reaction with UV light, as shown in Scheme 11. Many methyl-substituted compounds of formula (12) are commercially available.

Scheme 12

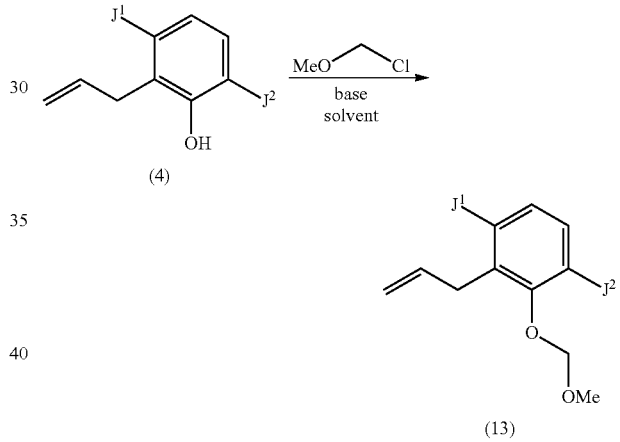

(4)

(13)

14) A compound of formula (13) where $J^1$ and $J^2$ are as defined in 1) can be made by reacting a phenol of formula (4) as defined in 3) with chloromethyl methyl ether and a base [such as sodium hydride or potassium carbonate] in a solvent [such as tetrahydrofuran or acetone], at a temperature between −20° C. and 80° C., as shown in Scheme 12.

Scheme 13

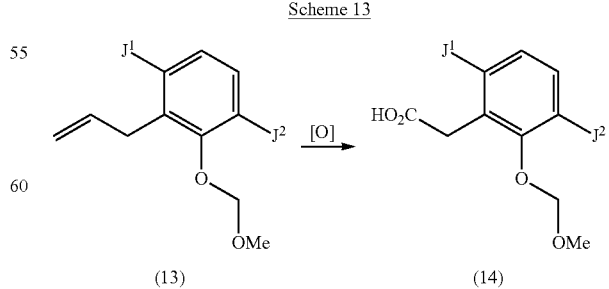

(13)            (14)

15) An acid of formula (14) where $J^1$ and $J^2$ are as defined in 1) can be made by reacting a compound of formula (13)

as defined in 14) with an oxidising agent [such as ruthenium tetroxide generated in-situ from sodium periodate and ruthenium (III) chloride] in a solvent system [comprising one or more of ethyl acetate, dichloromethane, water and acetonitrile] at a temperature between 0° C. and 50° C., as shown in Scheme 13.

16) An acid of formula (14) where $J^1$ and $J^2$ are as defined in 1) can be made by oxidising a compound of formula (13) as defined in 14) by a two-stage process known to the person skilled in the art as ozonolysis followed by Pinnick oxidation, via an intermediate aldehyde.

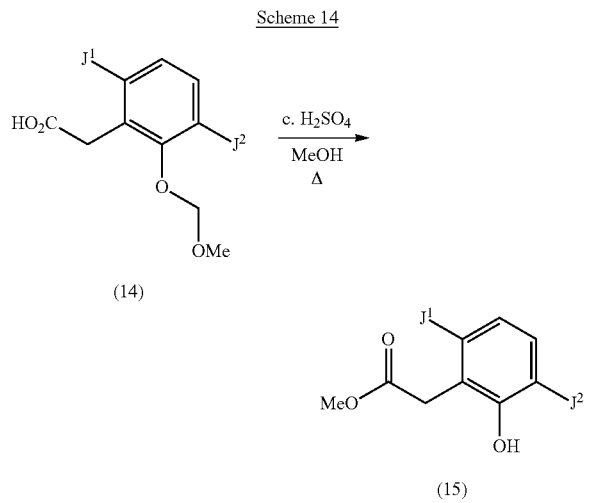

17) An ester of formula (15) where $J^1$ and $J^2$ are as defined in 1) can be made by reacting an acid of formula (14) as defined in 15) with methanol and concentrated sulfuric acid, at a temperature between 0° C. and reflux, as shown in Scheme 14.

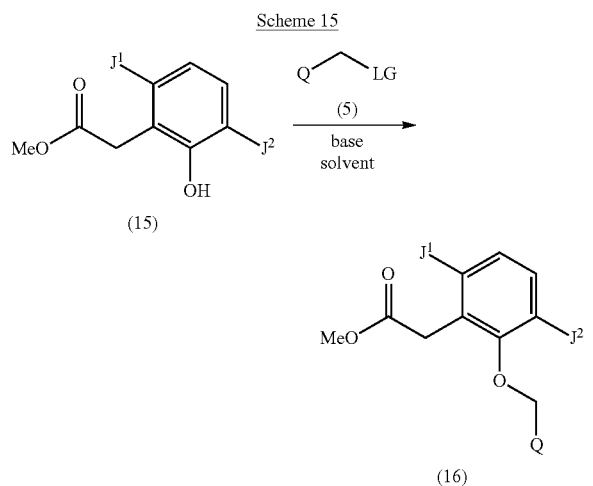

18) A compound of formula (16) where $J^1$ and $J^2$ are as defined in 1) can be made by reacting an ester of formula (15) as defined in 17) with a compound of formula (5) where LG is a leaving group, for example a halide [such as chloride, bromide or iodide], tosylate, mesylate or triflate, in the presence of a base [such as potassium carbonate] in a solvent [such as acetone or acetonitrile] and optionally using heating, as shown in Scheme 15. Many compounds of formula (5) are commercially available [such as 2-(bromomethyl)pyridine, 3-(bromomethyl)pyridine, 2-chloro-5-chloromethylthiazole or 2-(chloromethyl)-1,3-thiazole] or can be made according to Scheme 11.

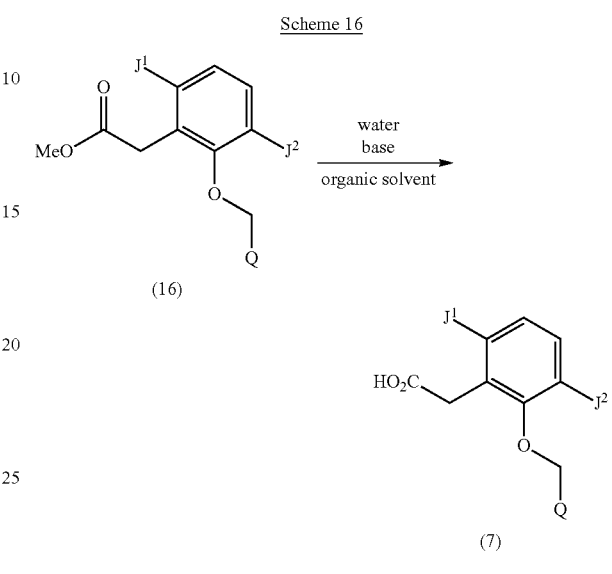

19) A carboxylic acid of formula (7) where $J^1$ and $J^2$ are as defined in 1) can be made by hydrolyzing a compound of formula (16) as defined in 18) with water and a base [such as lithium hydroxide, sodium hydroxide or potassium hydroxide] in the presence of an organic solvent [such as tetrahydrofuran, methanol or ethanol], at a temperature between 0° C. and 80° C., as shown in Scheme 16.

The compounds according to the invention can be used as herbicidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%

Dusts:
active ingredient: 0.1 to 10%, preferably 0.1 to 5%
solid carrier: 99.9 to 90%, preferably 99.9 to 99%

Suspension Concentrates:
active ingredient: 5 to 75%, preferably 10 to 50%
water: 94 to 24%, preferably 88 to 30%
surface-active agent: 1 to 40%, preferably 2 to 30%

Wettable Powders:
active ingredient: 0.5 to 90%, preferably 1 to 80%
surface-active agent: 0.5 to 20%, preferably 1 to 15%
solid carrier: 5 to 95%, preferably 15 to 90%

Granules:
active ingredient: 0.1 to 30%, preferably 0.1 to 15%
solid carrier: 99.5 to 70%, preferably 97 to 85%

The following Examples further illustrate, but do not limit, the invention:

| Wettable powders | a) | b) | c) |
| --- | --- | --- | --- |
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
| --- | --- | --- | --- |
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Emulsifiable concentrate | |
| --- | --- |
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
| --- | --- | --- | --- |
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
| --- | --- |
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
| --- | --- |
| Active ingredients | 8% |
| polyethylene glycol (mol. wt. 200) | 3% |
| Kaolin | 89% |

The finely ground combination is uniformly applied, in a mixer, to the Kaolin moistened with polyethylene glycol. Non-dusty coated granules are obtained in this manner.

| Suspension concentrate | |
| --- | --- |
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
| --- | --- |
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

The composition of the present may further comprise at least one additional pesticide. For example, the compounds according to the invention can also be used in combination with other herbicides or plant growth regulators. In a preferred embodiment the additional pesticide is a herbicide and/or herbicide safener.

Thus, compounds of formula (I) can be used in combination with one or more other herbicides to provide various herbicidal mixtures. Specific examples of such mixtures include (wherein "I" represents a compound of formula (I)):—I+acetochlor; I+acifluorfen-sodium; I+aclonifen; I+alachlor; I+alloxydim; I+ametryn; I+amicarbazone; I+amidosulfuron; I+aminocyclopyrachlor; I+aminopyralid; I+amitrole; I+asulam; I+atrazine; I+bensulfuron-methyl; I+bentazone; I+bicyclopyrone; I+bifenox; I+bispyribac-sodium; I+bromacil; I+bromoxynil; I+butafenacil; I+cafenstrole; I+carfentrazone-ethyl; I+chlorimuron-ethyl; I+chlorotoluron; I+cinosulfuron; I+clethodim; I+clodinafop-propargyl; I+clomazone; I+clopyralid; I+cyhalofop-butyl; I+2,4-D (including the choline salt and 2-ethylhexyl ester thereof); I+daimuron; I+desmedipham; I+dicamba (including the aluminum, aminopropyl, bis-aminopropylmethyl, choline, diglycolamine, dimethylamine, dimethylammonium, potassium and sodium salts thereof); I+diclofop-methyl; I+difenzoquat; I+diflufenican; I+diflufenzopyr; I+dimethachlor; I+dimethenamid-P; I+diquat dibromide; I+diuron; I+esprocarb; I+ethofumesate; I+fenoxaprop-P-ethyl; I+fenquinotrione; I+flazasulfuron; I+florasulam; I+fluazifop-P-butyl; I+flucarbazone-sodium; I+flufenacet; I+flumetralin; I+flumetsulam; I+flumioxazin; I+flupyrsulfuron-methyl-sodium; I+fluroxypyr-meptyl; I+fluthiacet-methyl; I+fomesafen; I+foramsulfuron; I+glufosinate (including the ammonium salt thereof); I+glyphosate (including the diammonium, isopropylammonium and potassium salts thereof); I+halauxifen-methyl; I+halosulfuron-methyl; I+haloxyfop-methyl; I+hexazinone; I+imazamox; I+imazapic; I+imazapyr; I+imazaquin; I+imazethapyr; I+indaziflam; I+iodosulfuron-methyl-sodium; I+iofensulfuron; I+iofensulfuron-sodium; I+ioxynil; I+ipfencarbazone; I+isoxaben; I+isoxaflutole; I+lactofen; I+linuron; I+mecoprop-P; I+mefenacet; I+mesosulfuron; I+mesosulfuron-methyl; I+mesotrione; I+metamitron; I+metobromuron; I+metolachlor; I+metoxuron; I+metribuzin; I+metsulfuron; I+molinate; I+napropamide; I+nicosulfuron; I+norflurazon; I+orthosulfamuron; I+oxadiargyl; I+oxadiazon; I+oxyfluorfen; I+paraquat dichloride; I+pendimethalin; I+penoxsulam; I+phenmedipham; I+picloram; I+picolinafen; I+pinoxaden; I+pretilachlor; I+primisulfuron-methyl; I+prodiamine; I+prometryn; I+propachlor; I+propanil; I+propaquizafop; I+propham; I+propyzamide; I+prosulfocarb; I+prosulfuron; I+pyrasulfotole; I+pyrazolynate, I+pyrazosulfuron-ethyl; I+pyribenzoxim; I+pyridate; I+pyriftalid; I+pyrithiobac-sodium; I+pyroxasulfone; I+pyroxsulam; I+quinclorac; I+quizalofop-P-ethyl; I+rimsulfuron; I+saflufenacil; I+sethoxydim; I+S-metolachlor; I+sulcotrione; I+sulfentrazone; I+tebuthiuron; I+tefuryltrione; I+tembotrione; I+terbuthylazine; I+terbutryn; I+thiencarbazone; I+thifensulfuron; I+tiafenacil; I+tolpyralate; I+topramezone; I+tralkoxydim; I+triafamone; I+triasulfuron; I+tribenuron-methyl; I+triclopyr; I+trifloxysulfuron-sodium; I+trifludimoxazin and tritosulfuron.

Especially preferred examples of such mixtures include:—I+ametryn; I+atrazine; I+bicyclopyrone; I+butafenacil; I+chlorotoluron; I+clodinafop-propargyl; I+clomazone; I+2,4-D (including the choline salt and 2-ethylhexyl ester thereof); I+dicamba (including the aluminum, aminopropyl, bis-aminopropylmethyl, choline, diglycolamine, dimethylamine, dimethylammonium, potassium and sodium salts thereof); I+dimethachlor; I+diquat dibromide; I+fluazifop-P-butyl; I+flumetralin; I+fomesafen; I+glufosinate-ammonium; I+glyphosate (including the diammonium, isopropylammonium and potassium salts thereof); I+mesotrione; I+molinate; I+napropamide; I+nicosulfuron; I+paraquat dichloride; I+pinoxaden; I+pretilachlor; I+primisulfuron-methyl; I+prometryn; I+prosulfocarb; I+prosulfuron; I+pyridate; I+pyriftalid; I+pyrazolynate, I+S-metolachlor; I+terbuthylazine; I+terbutryn; I+tralkoxydim; I+triasulfuron and I+trifloxysulfuron-sodium.

Preferred herbicide mixture products for weed control in cereals (especially wheat and/or barley) include:—I+amidosulfuron; I+aminopyralid; I+bromoxynil; I+carfentrazone-ethyl; I+chlorotoluron; I+clodinafop-propargyl; I+clopyralid; I+2,4-D (including the choline salt and 2-ethylhexyl ester thereof); I+dicamba (including the aluminum, aminopropyl, bis-aminopropylmethyl, choline, diglycolamine, dimethylamine, dimethylammonium, potassium and sodium salts thereof); I+difenzoquat; I+diflufenican; I+fenoxaprop-P-ethyl; I+florasulam; I+flucarbazone-sodium; I+flufenacet; flupyrsulfuron-methyl-sodium; I+fluroxypyr-meptyl; I+halauxifen-methyl; I+iodosulfuron-methyl-sodium; I+iofensulfuron; I+iofensulfuron-sodium; I+mesosulfuron; I+mesosulfuron-methyl; I+metsulfuron; I+pendimethalin; I+pinoxaden; I+prosulfocarb; I+pyrasulfotole; I+pyroxasulfone; I+pyroxsulam; I+topramezone; I+tralkoxydim; I+triasulfuron and I+tribenuron-methyl.

Preferred herbicide mixture products for weed control in corn include:—I+acetochlor; I+alachlor; I+atrazine; I+bicyclopyrone; I+2,4-D (including the choline salt and 2-ethylhexyl ester thereof); I+dicamba (including the aluminum, aminopropyl, bis-aminopropylmethyl, choline, diglycolamine, dimethylamine, dimethylammonium, potassium and sodium salts thereof); I+diflufenzopyr; I+dimethenamid-P; I+flumioxazin; I+fluthiacet-methyl; I+foramsulfuron; I+glufosinate (including the ammonium salt thereof); I+glyphosate (including the diammonium, isopropylammonium and potassium salts thereof); I+isoxaflutole; I+mesotrione; I+nicosulfuron; I+primisulfuron-methyl; I+prosulfuron; I+pyroxasulfone; I+rimsulfuron; I+S-metolachlor, I+terbuthylazine; I+tembotrione; I+thiencarbazone and I+thifensulfuron.

Preferred herbicide mixture products for weed control in rice include:—I+2,4-D; I+2,4-D choline salt; I+2,4-D-2- ethylhexyl ester; I+bensulfuron-methyl; I+bispyribac-sodium; I+cafenstrole; I+cinosulfuron; I+clomazone; I+cyhalofop-butyl; I+daimuron; I+dicamba (including the aluminum, aminopropyl, bis-aminopropylmethyl, choline, diglycolamine, dimethylamine, dimethylammonium, potassium and sodium salts thereof); I+esprocarb; I+fenoxaprop-P-ethyl; I+florasulam; I+halauxifen-methyl; I+halosulfuron-methyl; I+iofensulfuron; I+ipfencarbazone; I+mefenacet; I+mesotrione; I+metsulfuron; I+molinate; I+orthosulfamuron; I+oxadiargyl; I+oxadiazon; I+pendimethalin; I+penoxsulam; I+pretilachlor; I+pyrazolynate; I+pyrazosulfuron-ethyl; I+pyribenzoxim; I+pyriftalid; I+quinclorac; I+tefuryltrione; I+triafamone and I+triasulfuron.

Preferred herbicide mixtures for weed control in soybean include:—I+acifluorfen-sodium; I+ametryn; I+atrazine; I+bentazone; I+bicyclopyrone; I+bromoxynil; I+carfentrazone-ethyl; I+chlorimuron-ethyl; I+clethodim; I+clomazone; I+2,4-D (including the choline salt and 2-ethylhexyl ester thereof); I+dicamba (including the aluminum, aminopropyl, bis-aminopropylmethyl, choline, diglycolamine, dimethylamine, dimethylammonium, potassium and sodium salts thereof); I+diquat dibromide; I+diuron; I+fenoxaprop-P-ethyl; I+fluazifop-P-butyl; I+flufenacet; I+flumioxazin; I+fomesafen; I+glufosinate (including the ammonium salt thereof); I+glyphosate (including the diammonium, isopropylammonium and potassium salts thereof); I+imazethapyr; I+lactofen; I+mesotrione; I+metolachlor; I+metribuzin; I+nicosulfuron; I+oxyfluorfen; I+paraquat dichloride; I+pendimethalin; I+pyroxasulfone; I+quizalofop-P-ethyl; I+saflufenacil; I+sethoxydim; I+S-metolachlor and I+sulfentrazone.

The mixing partners of the compound of formula (I) may also be in the form of esters or salts, as mentioned e.g. in The Pesticide Manual, Fourteenth Edition, British Crop Protection Council, 2006.

The compound of formula (I) can also be used in mixtures with other agrochemicals such as fungicides, nematicides or insecticides, examples of which are given in The Pesticide Manual.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula I with the mixing partner).

Compounds of formula (I) of the present invention may also be combined with herbicide safeners. Preferred combinations (wherein "I" represents a compound of Formula (I)) include:—I+benoxacor, I+cloquintocet-mexyl; I+cyprosulfamide; I+dichlormid; I+fenchlorazole-ethyl; I+fenclorim; I+fluxofenim; 1+furilazole I+isoxadifen-ethyl; I+mefenpyr-diethyl; I+N-(2-methoxybenzoyl)-4-[(methylaminocarbonyl)amino] benzenesulfonamide and I+oxabetrinil.

Particularly preferred are mixtures of a compound of Formula I with cyprosulfamide, isoxadifen-ethyl, cloquintocet-mexyl and/or N-(2-methoxybenzoyl)-4-[(methylaminocarbonyl)amino]benzenesulfonamide.

The safeners of the compound of formula (I) may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of formula (I) to safener is from 100:1 to 1:10, especially from 20:1 to 1:1.

The mixtures can advantageously be used in the above-mentioned formulations (in which case "active ingredient" relates to the respective mixture of compound of formula (I) with the safener).

The compounds of formula (I) of this invention are useful as herbicides. The present invention therefore further comprises a method for controlling unwanted plants comprising applying to the said plants or a locus comprising them, an effective amount of a compound of the invention or a herbicidal composition containing said compound. 'Controlling' means killing, reducing or retarding growth or preventing or reducing germination. Generally the plants to be controlled are unwanted plants (weeds). 'Locus' means the area in which the plants are growing or will grow.

The rates of application of compounds of formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. In a particularly preferred aspect, the crop plant has been engineered to over-express homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

Compounds of formula I and compositions of the invention can typically be used to control a wide variety of monocotyledonous and dicotyledonous weed species. Examples of monocotyledonous species that can typically be controlled include *Alopecurus myosuroides, Avena fatua, Brachiaria plantaginea, Bromus tectorum, Cyperus esculentus, Digitaria sanguinalis, Echinochloa crus-galli, Lolium perenne, Lolium multiflorum, Panicum miliaceum, Poa annua, Setaria viridis, Setaria faberi* and *Sorghum bicolor*. Examples of dicotyledonous species that can be controlled include *Abutilon theophrasti, Amaranthus retroflexus, Bidens pilosa, Chenopodium album, Euphorbia heterophylla, Galium aparine, Ipomoea hederacea, Kochia scoparia, Polygonum convolvulus, Sida spinosa, Sinapis arvensis, Solanum nigrum, Stellaria media, Veronica persica* and *Xanthium strumarium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

Various aspects and embodiments of the present invention will now be illustrated in more detail by way of example. It will be appreciated that modification of detail may be made without departing from the scope of the invention.

PREPARATION EXAMPLES

Example 1

Preparation of 7-[3,6-dichloro-2-[(2-chlorothiazol-5-yl)methoxy]phenyl]-8-hydroxy-5-prop-2-ynyl-pyrido[2,3-b]pyrazin-6-one

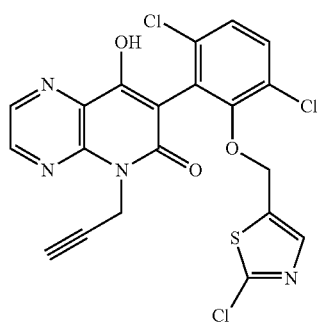 [SMILES: C#CCn1c(=O)c(-c2c(Cl)ccc(Cl)c2OCc2cnc(Cl)s2)c(O)c2nccnc21]

1.1 2-allyloxy-1,4-dichloro-benzene

To a stirred solution of 2,5-dichlorophenol (50 g, 307 mmol) in acetone (300 mL) under $N_2$ was added potassium carbonate (42.4 g, 337 mmol) and the mixture stirred at room temperature for 10 min. Allyl bromide (41 g, 337 mmol) was added and the reaction heated at 60° C. for 4 h. The mixture was cooled to room temperature and filtered, the residue washed with acetone (300 ml) and the combined filtrate was concentrated under reduced pressure to afford 2-allyloxy-1,4-dichloro-benzene as a yellow oil (60 g, 96%), which was progressed without further purification.

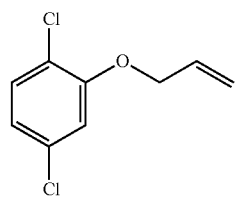

$^1$H NMR (400 MHz, CDCl$_3$): δ: 7.27 (d, J=8.3, 1 H,), 6.89-6.86 (m, 2H), 6.09-5.99 (m, 1 H), 5.46 (d, J=17.3, 1H), 5.33 (d, J=10.6, 1H), 4.59 (d, J=4.9, 2H).

1.2 2-allyl-3,6-dichloro-phenol

A stirred solution of 2-allyloxy-1,4-dichloro-benzene (60 g, 295 mmol) in N,N-dimethylaniline (200 ml) was heated at a temperature between 190° C. and 200° C. for 18 h. The reaction mixture was cooled to room temperature, poured into 30% hydrochloric acid (200 ml) and extracted with ethyl acetate (3×200 ml). The combined organics were washed with 30% hydrochloric acid (100 ml×4), followed by water and finally brine. The organics were dried over sodium sulfate, filtered and concentrated to give 2-allyl-3,6-dichloro-phenol (58 g, 96%).

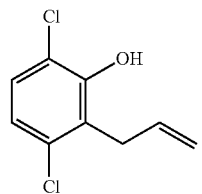

$^1$H NMR (400 MHz, CDCl$_3$): δ: 9.69 (s, 1 H,), 7.27 (d, J=8.6, 1H), 6.96 (d, J=8.6, 1 H), 5.9-5.8 (m, 1H), 5.05-4.91 (m, 2H), 3.5 (d, J=6, 2H).

1.3 2-allyl-1,4-dichloro-3-(methoxymethoxy)benzene

Dry sodium hydride (15 g, 60% in mineral oil, 369 mmol) was suspended in tetrahydrofuran (250 mL) and cooled to 0° C. under nitrogen. 2-allyl-3,6-dichloro-phenol (50 g, 246 mmol) was dissolved in tetrahydrofuran (250 mL) and added dropwise to the sodium hydride suspension over 30 min. The reaction mixture was then allowed to stir at room temperature for a further 2 h. Chloromethyl methyl ether (56 ml, 59 g, 739 mmol) was then added over 30 min and the reaction stirred for a further 2 h.

The reaction mixture was concentrated in vacuo and the residue partitioned between ethyl acetate and 0.1M sodium hydroxide. The aqueous layer was extracted with ethyl acetate (×2). The organic layers were combined, washed with 0.1M sodium hydroxide, then with brine, dried over sodium sulfate, and concentrated under reduced pressure to afford 2-allyl-1,4-dichloro-3-(methoxymethoxy)benzene (55 g, 90%).

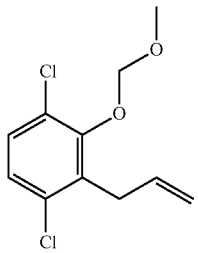

¹H NMR (400 MHz, CDCl₃): δ: 7.20 (d, J=8.6, 1H), 7.11 (d, J=8.6, 1H), 5.99-5.89 (m, 1H), 5.09-4.99 (m, 4H), 3.63 (s, 5H).

1.4 2-[3,6-dichloro-2-(methoxymethoxy)phenyl]acetic acid

In a 10 L reaction flask, a mixture of 2-allyl-1,4-dichloro-3-(methoxymethoxy)benzene (55 g, 223 mmol), dichloromethane (680 ml), acetonitrile (680 ml) and water (1000 ml) was cooled to 0° C. using an ice-salt bath. Ruthenium (III) chloride (8.7 g, 33.4 mmol) was added to the stirred biphasic mixture. Sodium periodate (338 g, 1.11 mol) was slowly added in small lots maintaining the temperature of the reaction mass below 5° C. (an exotherm of between 10° C. and 12° C. was observed). The reaction mass was allowed to warm to room temperature and stirred for an additional 4 h. The mixture was filtered through celite and then phase separated. The aqueous layer was extracted with additional dichloromethane (3×1000 ml). The combined organics were washed with saturated sodium metabisulfite solution (3×500 ml) then brine (500 ml). Evaporation in vacuo afforded 2-[3,6-dichloro-2-(methoxymethoxy)phenyl]acetic acid (50 g, 84%) in acceptable purity.

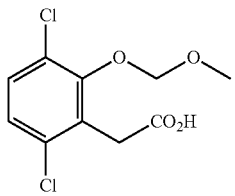 [SMILES: COCOc1c(Cl)ccc(Cl)c1CC(=O)O]

¹H NMR (400 MHz, CDCl₃): δ: 7.28 (d, J=8.6, 1H), 7.14 (d, J=8.6, 1H), 5.10 (s, 2H), 3.97 (s, 2H), 3.59 (s, 3H).

1.5 methyl 2-(3,6-dichloro-2-hydroxy-phenyl)acetate

2-[3,6-dichloro-2-(methoxymethoxy)phenyl]acetic acid (50 g, 189 mmol) in methanol (450 mL) was stirred at a temperature between 0° C. and 5° C. Conc. sulphuric acid (4 mL) was added slowly to the methanolic solution over a period of 20 min. The reaction mass was then slowly heated to reflux over a period of 3 h. The reaction was monitored by thin layer chromatography and when judged complete, methanol was distilled out under reduced pressure and the residue poured into saturated aqueous sodium bicarbonate solution. The aqueous layer was extracted with ethyl acetate and the combined organics washed with brine. The organics were concentrated to afford crude product. The crude product was purified by trituration with ethyl acetate-hexane to obtain methyl 2-(3,6-dichloro-2-hydroxy-phenyl)acetate (32 g, 72%) as an off-white solid.

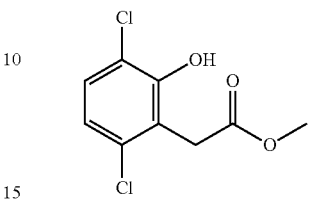

¹H NMR (400 MHz, CDCl₃): δ: 7.19 (d, J=8.7, 1H), 6.94 (d, J=8.6, 1H), 6.14 (bs, 1H), 3.89 (s, 2H), 3.72 (s, 3H).

1.6 methyl 2-[3,6-dichloro-2-[(2-chlorothiazol-5-yl)methoxy]phenyl]acetate

To a stirred solution of methyl 2-(3,6-dichloro-2-hydroxyphenyl)acetate (15 g, 63.8 mmol) in acetone (450 mL) was added potassium carbonate (13.2 g, 95.7 mmol). 2-Chloro-5-chloromethylthiazole (11.8 g, 70.2 mmol) in acetone (450 mL) was added dropwise. After completion of the addition the reaction was stirred at room temperature for 6 h. Solids were removed by filtration and the filtrate evaporated under reduced pressure to give crude product. Purification by flash column chromatography gave methyl 2-[3,6-dichloro-2-[(2-chlorothiazol-5-yl)methoxy]phenyl]acetate (14.5 g, 62%).

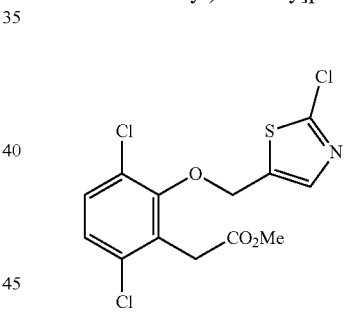

¹H NMR (400 MHz, CDCl₃): δ: 7.51 (s, 1H), 7.30 (d, J=8.6, 1H), 7.17 (d, J=8.7, 1H), 5.15 (s, 2H), 3.83 (s, 2H), 3.72 (s, 3H).

1.7 2-[3,6-dichloro-2-[(2-chlorothiazol-5-yl)methoxy]phenyl]acetic acid

To a stirred solution of methyl 2-[3,6-dichloro-2-[(2-chlorothiazol-5-yl)methoxy]phenyl]acetate (14.5 g, 39.6 mmol) in tetrahydrofuran (75 mL) and water (75 mL) was added lithium hydroxide monohydrate. The reaction mixture was stirred at room temperature for 16 h. The organics were evaporated under reduced pressure and the aqueous residue acidified with 2N hydrochloric acid. The mixture was extracted with ethyl acetate (×3), the combined organics washed with brine, dried over sodium sulfate, filtered and evaporated to obtain 2-[3,6-dichloro-2-[(2-chlorothiazol-5-yl)methoxy]phenyl]acetic acid (12 g, 86%).

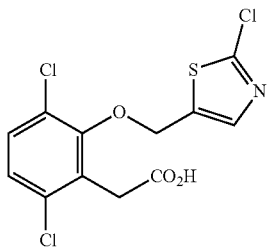 [SMILES: O=C(O)Cc1c(Cl)ccc(Cl)c1OCc1cnc(Cl)s1]

$^1$H NMR (400 MHz, DMSO-d6): δ: 12.67 (bs, 1H), 7.78 (s, 1H), 7.52 (d, J=8.7, 1H), 7.36 (d, J=8.6, 1H), 5.20 (s, 2H), 3.75 (s, 2H).

1.8 methyl 3-[[2-[3,6-dichloro-2-[(2-chlorothiazol-5-yl)methoxy]phenyl]acetyl]amino]pyrazine-2-carboxylate A stirred solution of 2-[3,6-dichloro-2-[(2-chlorothiazol-5-yl)methoxy]phenyl]acetic acid (1.00 g, 2.84 mmol, 1 eq.) in dichloromethane (10 mL) was treated with N,N-dimethylformamide (0.05 mL) and cooled in an ice-water bath. Oxalyl chloride (0.5 mL, 5.96 mmol, 2.1 eq.) was added dropwise and the reaction mixture was stirred at room temperature for 1 h.

The reaction mixture was evaporated to dryness and the residue re-dissolved in dichloromethane (10 mL). Separately, methyl 3-aminopyrazine-2-carboxylate (369 mg, 2.41 mmol, 0.85 eq.) was dissolved in dichloromethane (10 mL) and pyridine (0.6 mL, 8.52 mmol, 3eq.) and cooled to 0° C. The acid chloride solution was added dropwise to the amine solution, with stirring, at 0° C. After completion of the addition, the reaction mixture was stirred at room temperature for 2 h.

The reaction mixture was diluted with dichloromethane then washed with 1N hydrochloric acid, saturated sodium bicarbonate solution, water and finally brine. The organics were dried over sodium sulfate, filtered and evaporated in vacuo to give a crude residue. Purification by flash column chromatography gave impure product which was triturated with 20% ether in hexane to obtain methyl 3-[[2-[3,6-dichloro-2-[(2-chlorothiazol-5-yl)methoxy]phenyl]acetyl]amino]pyrazine-2-carboxylate (770 mg, 55%) as an off-white solid.

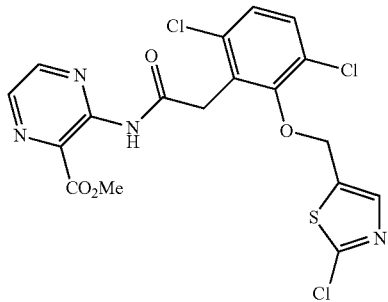 [SMILES: COC(=O)c1nccnc1NC(=O)Cc1c(Cl)ccc(Cl)c1OCc1cnc(Cl)s1]

$^1$H NMR (400 MHz, CDCl$_3$): δ: 10.88 (br. s, 1H), 8.59 (s, 1H), 8.42 (s, 1H), 7.51 (s, 1H), 7.33 (d, J=8.6, 1H), 7.20 (d, J=8.8, 1H), 5.24 (s, 2H), 4.19 (s, 2H), 4.04 (s, 3H).

1.9 [7-[3,6-dichloro-2-[(2-chlorothiazol-5-yl)methoxy]phenyl]-6-oxo-5H-pyrido[2,3-b]pyrazin-8-yl]2-methylpropanoate To a stirred solution of methyl 3-[[2-[3,6-dichloro-2-[(2-chlorothiazol-5-yl)methoxy]phenyl]acetyl]amino]pyrazine-2-carboxylate (670 mg, 1.37 mmol, 1 eq.) in anhydrous tetrahydrofuran (13 mL) was added 1M lithium hexamethyldisilazide (4.1 mL, 4.1 mmol, 3 eq.) dropwise at 0° C. After completion of the addition, the reaction mixture was stirred at room temperature for 15 h.

The reaction was cooled in an ice bath and quenched with 2N hydrochloric acid. The mixture was extracted with ethyl acetate (×2). The combined organics were washed with brine, dried over sodium sulfate, filtered and evaporated under reduced pressure to give 7-[3,6-dichloro-2-[(2-chlorothiazol-5-yl)methoxy]phenyl]-8-hydroxy-5H-pyrido[2,3-b]pyrazin-6-one (600 mg, 96%).

To a stirred solution of 7-[3,6-dichloro-2-[(2-chlorothiazol-5-yl)methoxy]phenyl]-8-hydroxy-5H-pyrido[2,3-b]pyrazin-6-one (680 mg, 1.4 mmol, 1 eq.) in dichloromethane (5 mL) was added pyridine (0.18 mL, 2.24 mmol, 1.5 eq.) and 4-(dimethylamino)pyridine [DMAP] (18 mg, 0.15 mmol, 0.1 eq.). The mixture was cooled in an ice bath, treated with isobutyryl chloride (0.2 mL, 2.1 mmol, 1.4 eq.), and stirred at room temperature for 3 h.

The reaction mixture was diluted with dichloromethane, then washed with 0.5 N hydrochloric acid, water, and finally brine. The organics were dried over sodium sulfate, filtered and evaporated in vacuo to obtain crude product. The crude was purified by flash column chromatography to obtain [7-[3,6-dichloro-2-[(2-chlorothiazol-5-yl)methoxy]phenyl]-6-oxo-5H-pyrido[2,3-b]pyrazin-8-yl]2-methylpropanoate (300 mg, 38%).

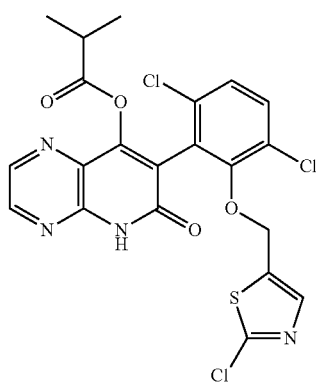 [SMILES: CC(C)C(=O)Oc1c(-c2c(Cl)ccc(Cl)c2OCc2cnc(Cl)s2)c(=O)[nH]c2nccnc12]

$^1$H NMR (400 MHz, CDCl$_3$): δ: 10.99 (br. s, 1H), 8.63 (s, 1H), 8.57 (s, 1H), 7.44 (d, J=8.7, 1H), 7.33 (s, 1H), 7.28 (d, J=8.7, 1H), 5.11-5.04 (m, 2H), 2.81-2.74 (m, 1H), 1.13 (d, J=6.9, 6H).

1.10 [7-[3,6-dichloro-2-[(2-chlorothiazol-5-yl)methoxy]phenyl]-6-oxo-5-prop-2-ynyl-pyrido[2,3-b]pyrazin-8-yl]2-methylpropanoate To a stirred suspension of sodium hydride (13 mg, 60% dispersed in oil, 0.31 mmol, 1.1 eq.) in N,N-dimethylformamide (2 mL) was added a solution of [7-[3,6-dichloro-2-[(2-chlorothiazol-5-yl)methoxy]phenyl]-6-oxo-5H-pyrido[2,3-b]pyrazin-8-yl]2-methylpropanoate (150 mg, 0.285 mmol, 1 eq.) in N,N-dimethylformamide (1 mL) dropwise at 0° C. After completion of the addition, the reaction mixture was stirred at 0° C. for 1 h. Propargyl bromide (0.04 mL, 0.49 mmol, 1.7 eq.) was added and the reaction stirred at room temperature for a further 3 h.

The reaction mixture was then cooled to 0° C. and quenched with 2N hydrochloric acid. The mixture was diluted with water and extracted into ethyl acetate (×2). The combined organics were washed with brine, dried over sodium sulfate, filtered and evaporated to give a crude residue. Purification by flash column chromatography afforded [7-[3,6-dichloro-2-[(2-chlorothiazol-5-yl)methoxy]phenyl]-6-oxo-5-prop-2-ynyl-pyrido[2,3-b]pyrazin-8-yl]2-methylpropanoate (105 mg, 65%) as a yellow gum.

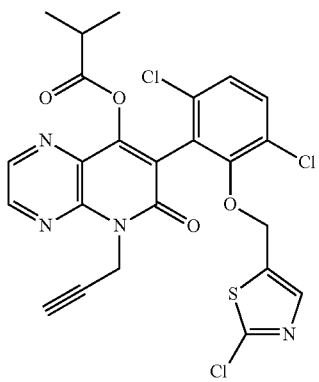 [SMILES: C#CCn1c(=O)c(-c2c(Cl)ccc(Cl)c2OCc2cnc(Cl)s2)c(OC(=O)C(C)C)c2nccnc21]

$^1$H NMR (400 MHz, CDCl$_3$): δ: 8.67 (s, 1H), 8.56 (s, 1H), 7.43 (d, J=8.6, 1H), 7.31-7.29 (m, 2H), 5.32-5.21 (m, 2H), 5.11-5.03 (m, 2H), 2.81-2.76 (m, 1H), 2.17 (s, 1H), 1.14-1.12 (m, 6H).

1.11 7-[3,6-dichloro-2-[(2-chlorothiazol-5-yl)methoxy]phenyl]-8-hydroxy-5-prop-2-ynyl-pyrido[2,3-b]pyrazin-6-one To the stirred suspension of [7-[3,6-dichloro-2-[(2-chlorothiazol-5-yl)methoxy]phenyl]-6-oxo-5-prop-2-ynyl-pyrido[2,3-b]pyrazin-8-yl]2-methylpropanoate (500 mg, 0.887 mmol, 1 eq.) in tetrahydrofuran (4 mL) and water (4 mL) at 0° C. was added potassium hydroxide (75 mg, 1.33 mmol, 1.5 eq.). The mixture was stirred at room temperature for 3 h. The reaction was then acidified with 2N hydrochloric acid and extracted with ethyl acetate (×2). The combined organics were washed with brine, dried over sodium sulfate, filtered and evaporated to obtain crude product. Purification by flash column chromatography gave 7-[3,6-dichloro-2-[(2-chlorothiazol-5-yl)methoxy]phenyl]-8-hydroxy-5-prop-2-ynyl-pyrido[2,3-b]pyrazin-6-one (290 mg, 66%) as a light-yellow solid.

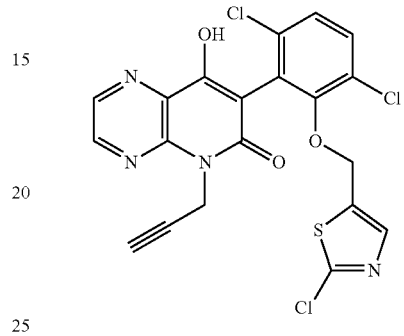

$^1$H NMR (400 MHz, DMSO-d6): δ: 12.02 (br. s, 1H), 8.89 (s, 1H), 8.72 (s, 1H), 7.64 (d, J=8.6, 1H), 7.46-7.45 (m, 2H), 5.14-5.01 (m, 4H), 3.13 (s, 1H).

Table 23 Preparation examples of compounds of formula (I), wherein A$_2$ is NR$^4$, A$_3$ is C(O), G is hydrogen, X is Cl and is ortho with respect to the bicyclic moiety, Y is Cl and is ortho with respect to the Q-CH$_2$O— moiety, and Q is

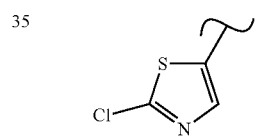

wherein ~ denotes the point of attachment to the rest of the molecule, and A$_1$ and R$^4$ are as shown in the table.

| Compound | A$_1$ | R$^4$ | NMR details |
|---|---|---|---|
| 1.19 | CH | HC≡C—CH$_2$— | $^1$H NMR (400 MHz, DMSO-d6) δ$_H$: 11.19 (bs, 1H), 8.77-8.75 (m, 1H), 8.41-8.39 (m, 1H), 7.62 (d, J = 8.7, 1H), 7.46 (d, J = 6.7, 1H), 7.42-7.39 (m, 2H), 5.11 (s, 2H), 5.05 (s, 2H), 3.01 (s, 1H). |
| 3.19 | CH | F$_2$CH—CH$_2$— | $^1$H NMR (400 MHz, DMSO-d6) δ$_H$: 11.28 (bs, 1H), 8.73 (d, J = 4.2, 1H), 8.41 (d, J = 7.7, 1H), 7.63 (d, J = 8.6, 1H), 7.45-7.42 (m, 3H), 6.33 (m, 1H), 5.04 (s, 2H), 4.87-4.80 (m, 2H). |
| 9.19 | N | HC≡C—CH$_2$— | $^1$H NMR (400 MHz, DMSO-d6) δ$_H$: 12.02 (bs, 1H), 8.89 (s, 1H), 8.72 (s, 1H), 7.64 (d, J = 8.6, 1H), 7.46-7.45 (m, 2H), 5.14-5.01 (m, 4H), 3.13 (s, 1H). |
| 11.19 | N | F$_2$CH—CH$_2$— | $^1$H NMR (400 MHz, DMSO-d6) δ$_H$: 12.09 (bs, 1H), 8.86 (s, 1H), 8.73 (s, 1H), 7.64 (d, J = 8.7, 1H), 7.46-7.45 (m, 2H), 6.48-6.20 (m, 1H), 5.11 (d, J = 12.7, 1H), 5.02 (d, J = 12.5, 1H), 4.85-4.78 (m, 2H). |
| 17.19 | C—OMe | HC≡C—CH$_2$— | $^1$H NMR (400 MHz, DMSO-d6) δ$_H$: 9.82 (s, 1H), 8.63 (d, J = 5.8, 1H), 7.60 (d, J = 8.7, 1H), 7.49 (s, 1H), 7.43 (d, J = 8.7, 1H), 7.11 (d, J = 5.8, 1H), 5.11-5.02 (m, 4H), 4.06 (s, 3H), 3.02 (s, 1H). |
| 19.19 | C—OMe | F$_2$CH—CH$_2$— | $^1$H NMR (400 MHz, DMSO-d6) δ$_H$: 9.88 (s, 1H), 8.60 (d, J = 5.8, 1H), 7.60 (d, J = 8.7, 1H), 7.47 (s, 1H), 7.43 (d, J = 8.7, 1H), 7.13 (d, J = 5.9, 1H), 6.46- |

-continued

| Compound | $A_1$ | $R^4$ | NMR details |
|---|---|---|---|
| | | | 6.18 (m, 1H), 5.10-5.01 (m, 2H), 4.88-4.80 (m, 2H), 4.06 (s, 3H). |

Table 24 Preparation examples of compounds of formula (I), wherein $A_2$ is $CR^{3a}R^{3b}$, $A_3$ is $S(O)_2$, G is hydrogen, X is Cl and is ortho with respect to the bicyclic moiety, Y is Cl and is ortho with respect to the Q-CH$_2$O— moiety, and Q is

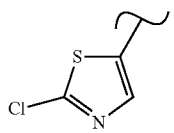

wherein ~ denotes the point of attachment to the rest of the molecule, and $A_1$, $R^{3a}$ and $R^{3b}$ are as shown in the table.

| Compound | $A_1$ | $R^{3a}$ | $R^{3b}$ | NMR details |
|---|---|---|---|---|
| 21.19 | N | CH$_3$ | CH$_3$ | $^1$H NMR (400 MHz, CDCl$_3$) $\delta_H$: 8.78 (d, J = 2.4 Hz, 1H), 8.63 (d, J = 2.4 Hz, 1H), 7.51-7.45 (m, 2H), 7.33 (d, J = 8.7 Hz, 1H), 5.31 (d, J = 3.4 Hz, 2H), 1.97 (s, 3H), 1.86 (s, 3H). |

BIOLOGICAL EXAMPLES

B1 Post-Emergence Efficacy

Seeds of a variety of test species are sown in standard soil in pots:—*Solanum nigrum* (SOLNI), *Amaranthus retoflexus* (AMARE), *Setaria faberi* (SETFA), *Alopecurus myosuroides* (ALOMY), *Echinochloa crus-galli* (ECHCG), *Ipomoea hederacea* (IPOHE), *Lolium perenne* (LOLPE). After 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethylene sorbitan monolaurate, CAS RN 9005-64-5). Compounds are applied at 1000 g/ha and 250 g/ha. The test plants are then grown in a glasshouse under controlled conditions in a glasshouse (at 24/16° C., day/night; 14 hours light; 65% humidity) and watered twice daily. After 13 days, the test is evaluated for the percentage damage caused to the plant. The biological activities are assessed on a five point scale (5=80-100%; 4=60-79%; 3=40-59%; 2=20-39%; 1=0-19%).

TABLE 25

Control of weed species by compounds of formula (I) after post-emergence application

| Compound | Application rate (g/ha) | AMARE | SOLNI | SETFA | LOLPE | ECHCG | IPOHE |
|---|---|---|---|---|---|---|---|
| 1.19 | 1000 | 5 | 5 | 5 | 5 | 5 | 5 |
| | 250 | 4 | 5 | 4 | 5 | 3 | 5 |
| 3.19 | 1000 | 5 | 5 | 5 | 5 | 4 | 5 |
| | 250 | 5 | 5 | 4 | 4 | 3 | 5 |
| 9.19 | 1000 | 5 | 5 | 5 | 5 | 5 | 5 |
| | 250 | 5 | 5 | 5 | 5 | 5 | 5 |
| 11.19 | 1000 | 5 | 5 | 5 | 5 | 4 | 5 |
| | 250 | 5 | 5 | 4 | 5 | 5 | 5 |
| 17.19 | 1000 | 5 | 5 | 5 | 5 | 5 | 5 |
| | 250 | 5 | 5 | 5 | 4 | 5 | 5 |
| 19.19 | 1000 | 5 | 5 | 5 | 5 | 5 | 5 |
| | 250 | 5 | 5 | 5 | 4 | 5 | 5 |

The invention claimed is:
1. A compound of Formula (I)

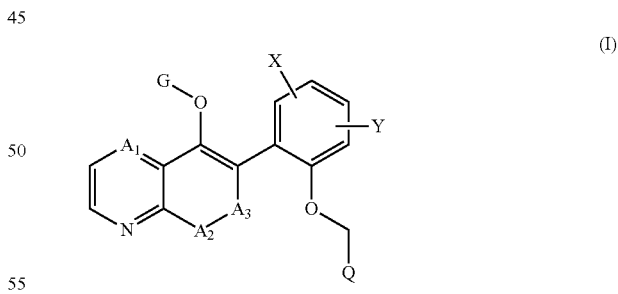

or a salt or N-oxide thereof;
wherein $A_1$ is $CR^1$ or N;
$R^1$ is hydrogen, $C_1$-$C_4$alkyl, $C_1$-$C_4$haloalkyl, $C_1$-$C_4$alkoxy, $C_1$-$C_4$alkylthio, halogen, cyano, or hydroxyl;
$A_2$ is $CR^{3a}R^{3b}$ or $NR^4$;
$A_3$ is C(O) or S(O)$_2$;
G is hydrogen, or C(O)$R^6$;
X and Y are each independently hydrogen, $C_1$-$C_3$alkyl, $C_1$-$C_3$alkoxy, $C_1$-$C_3$haloalkyl, $C_1$-$C_3$haloalkoxy, or halogen;

$R^{3a}$ and $R^{3b}$ are independently hydrogen, halogen, cyano, $C_1$-$C_8$alkyl, $C_1$-$C_8$alkoxy-$C_1$-$C_4$alkyl-, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkyl-, heterocyclyl, heterocyclyl-$C_1$-$C_4$alkyl-, or $C_1$-$C_8$alkoxycarbonyl-; or $R^{3a}$ and $R^{3b}$ together with the carbon atom they are attached to join to form a 3- to 10-membered carbocyclic ring or a 4- to 10-membered heterocyclic ring;

$R^4$ is hydrogen, $C_1$-$C_{10}$alkyl, $C_1$-$C_4$haloalkyl, $C_2$-$C_{10}$alkenyl, $C_2$-$C_4$haloalkenyl, $C_2$-$C_{10}$alkynyl, $C_2$-$C_4$haloalkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N-$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^{10}$, which may be the same or different, or heterocyclyl-$C_1$-$C_6$alkyl- or heterocyclyl-$C_1$-$C_6$alkyl- wherein the heterocyclyl moiety is substituted by one to three $R^{10}$, which may be the same or different;

$R^6$ is selected from the group consisting of $C_1$-$C_6$alkyl, $C_2$-$C_6$alkenyl, $C_2$-$C_6$alkynyl, $C_1$-$C_6$alkyl-S—, —$NR^7R^8$ and phenyl optionally substituted by one or more $R^9$;

$R^7$ and $R^8$ are independently selected from the group consisting of $C_1$-$C_6$ alkyl and $C_{1-6}$ alkoxy, or $R^7$ and $R^8$ together can form a morpholinyl ring; and, $R^9$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy; and each $R^{10}$ is independently halogen, $C_1$-$C_4$alkyl, $C_1$-$C_4$haloalkyl, $C_1$-$C_4$alkoxy or $C_1$-$C_4$haloalkoxy;

Q is (i), (ii) or (iii)

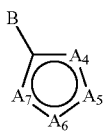

(i)

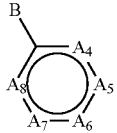

(ii)

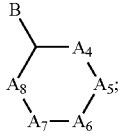

(iii)

wherein B designates the point of attachment to the rest of the molecule;

$A_4$, $A_5$, $A_6$, $A_7$, and $A_8$, are independently $CR^{11}$, $NR^{12}$, N, S, O, or C(O), provided that at least one and no more than three of $A_4$, $A_5$, $A_6$, $A_7$, and $A_8$ is N, $NR^{12}$, S, O, or C(O);

each $R^{11}$ is independently hydrogen, $C_1$-$C_4$alkyl, $C_1$-$C_4$haloalkyl, halogen, cyano, hydroxyl, $C_1$-$C_4$alkoxy, or $C_1$-$C_4$alkylthio;

each $R^{12}$ is independently hydrogen, $C_1$-$C_4$alkyl, $C_1$-$C_4$haloalkyl, hydroxyl, $C_1$-$C_4$alkoxy, or $C_1$-$C_4$alkylthio.

2. The compound of claim 1 wherein $R^4$ is hydrogen, $C_1$-$C_2$alkyl, $C_1$-$C_2$haloalkyl, $C_2$-$C_3$alkenyl or $C_2$-$C_3$alkynyl.

3. The compound of claim 1 wherein X is $C_1$-$C_3$alkyl, $C_1$-$C_3$alkoxy, $C_1$-$C_3$haloalkyl, $C_1$-$C_3$haloalkoxy, or halogen, and is ortho with respect to the bi-cyclic moiety.

4. The compound according to claim 1 wherein Y is hydrogen, $C_1$-$C_3$alkyl, $C_1$-$C_3$alkoxy, $C_1$-$C_3$haloalkyl, $C_1$-$C_3$haloalkoxy, or halogen, and is ortho with respect to the Q-$CH_2$O— moiety.

5. The compound according to claim 1 wherein $A_3$ is C(O).

6. The compound according to claim 1 wherein $A_3$ is $S(O)_2$.

7. The compound according to claim 1, wherein Q is an optionally substituted pyridyl, thiazolyl, oxazolyl, imidazolyl, isoxazolyl, isothiazolyl, pyrazolyl, pyrazinyl, pyridazinyl, pyrimidyl, or pyridone.

8. The compound according to claim 1, wherein any two of $A_4$, $A_5$, $A_6$, $A_7$, and $A_8$ are independently N, $NR^{12}$, S, O, or C(O) and all remaining $A_4$, $A_5$, $A_6$, $A_7$, and $A_8$ are $CR^{11}$.

9. The compound according to claim 1, wherein one of $A_4$, $A_5$, $A_6$, $A_7$, and $A_8$ is independently N and all remaining $A_4$, $A_5$, $A_6$, $A_7$, and $A_8$ are $CR^{11}$.

10. The compound according to claim 1 wherein Q is (i) and is selected from the group consisting of:

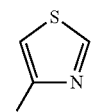

(i)-1

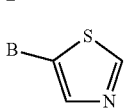

(i)-2

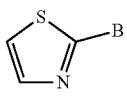

(i)-3

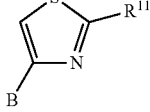

(i)-4

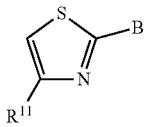

(i)-5

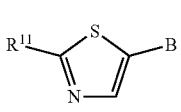

(i)-6

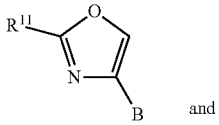

(i)-7 and

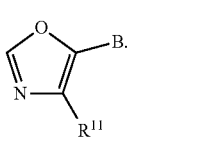

(i)-8

11. The compound according to claim 1 wherein Q is (ii) and is selected from the group consisting of:

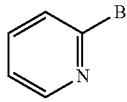 (ii)-1

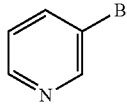 (ii)-2

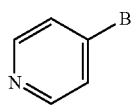 (ii)-3

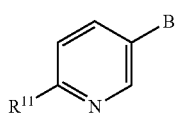 (ii)-4

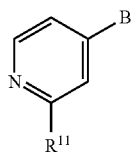 (ii)-5

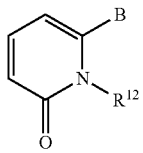 (ii)-6

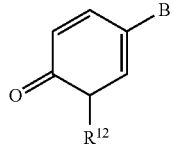 (ii)-7

-continued (ii)-8 and.

12. The compound according to claim 1, wherein $R^{11}$ is independently hydrogen, $C_1$-$C_4$alkyl, $C_1$-$C_4$haloalkyl, halogen, cyano, hydroxyl, $C_1$-$C_4$alkoxy, or $C_1$-$C_4$alkylthio.

13. The herbicidal composition comprising a herbicidal compound according to claim 1 and an agriculturally acceptable formulation adjuvant.

14. The herbicidal composition according to claim 13, further comprising at least one additional pesticide.

15. A method of controlling unwanted plant growth, comprising applying a compound of formula (I) as defined in claim 1 to the unwanted plants or to the locus thereof.

* * * * *